(12) United States Patent
Liu et al.

(10) Patent No.: US 12,194,162 B2
(45) Date of Patent: Jan. 14, 2025

(54) ABSORBENT ARTICLES COMPRISING SEMI-HYDROPHILIC COMPOSITIONS

(71) Applicant: The Procter & Gamble Company, Cincinnati, OH (US)

(72) Inventors: Zhe Liu, Beijing (CN); Gueltekin Erdem, Beijing (CN); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 870 days.

(21) Appl. No.: 17/149,780

(22) Filed: Jan. 15, 2021

(65) Prior Publication Data
US 2021/0220509 A1    Jul. 22, 2021

Related U.S. Application Data

(63) Continuation of application No. PCT/CN2020/072758, filed on Jan. 17, 2020.

(51) Int. Cl.
*A61L 15/22* (2006.01)
*A61F 13/511* (2006.01)
(Continued)

(52) U.S. Cl.
CPC ....... *A61L 15/225* (2013.01); *A61F 13/51121* (2013.01); *A61L 15/40* (2013.01);
(Continued)

(58) Field of Classification Search
CPC .. A61L 15/225; A61L 15/40; A61L 2300/802; A61L 15/34; A61L 15/24;
(Continued)

(56) References Cited

U.S. PATENT DOCUMENTS 6,296,862 B1 *  10/2001  Paul ................. A61L 15/46
                                                    604/367
6,440,437 B1 *  8/2002   Krzysik ............ A61K 8/062
                                                    424/443
(Continued)

FOREIGN PATENT DOCUMENTS

CN          1367674 A      9/2002
CN        101678144 A      3/2010
(Continued)

OTHER PUBLICATIONS

Anjana, Arata Hair Products Review- Shampoo, Condition, Hair Gel, Hair Cream, Oct. 15, 2019, Curly and Beauty Diary (Year: 2019).*

(Continued)

*Primary Examiner* — Philip R Wiest
*Assistant Examiner* — Brandon W. Levy
(74) *Attorney, Agent, or Firm* — Anna E. Haller; Christian M. Best

(57) ABSTRACT

An absorbent article having a topsheet with natural fibers and a semi-hydrophilic composition is provided. The semi-hydrophilic composition may have a wax ester and a polyglyceryl emulsifier in a ratio of between about 0.5:1 and 1.5:1. The topsheet may have a Contact Angle of between about 35° and about 100°. The topsheet may have a Fluid Strike-Through time of between about 0.5 seconds to about 18 seconds and a wicking height of between about 0 mm and about 10 mm.

20 Claims, 19 Drawing Sheets

(51) Int. Cl.
  *A61L 15/40* (2006.01)
  *A61F 13/51* (2006.01)

(52) U.S. Cl.
  CPC .............. *A61F 2013/51019* (2013.01); *A61F 2013/51038* (2013.01); *A61L 2300/802* (2013.01)

(58) Field of Classification Search
  CPC .......... A61L 15/60; A61L 15/48; A61L 15/46; A61L 15/50; A61L 15/56; A61F 13/51121; A61F 2013/51019; A61F 2013/51038; A61F 13/496; A61F 13/84; A61F 13/15203; A61F 13/565; A61F 13/551; A61F 13/5655; A61F 13/15617; A61F 13/15804; A61F 13/51113; A61F 2013/51117; A61F 13/511; A61F 2013/51073; A61F 13/15; A61Q 19/00
  See application file for complete search history.

(56) References Cited

U.S. PATENT DOCUMENTS

| | | | |
|---|---|---|---|
| 6,645,190 B1 | 11/2003 | Olson | |
| 6,761,711 B1 | 7/2004 | Fletcher | |
| 6,817,994 B2 | 11/2004 | Coenen | |
| 6,840,928 B2 | 1/2005 | Datta | |
| 6,849,067 B2 | 2/2005 | Fletcher | |
| 6,893,426 B1 | 5/2005 | Coenen | |
| 6,953,452 B2 | 10/2005 | Coenen | |
| 6,969,377 B2 | 11/2005 | Koele | |
| 7,156,833 B2 | 1/2007 | Couture-dorschner | |
| 7,201,744 B2 | 4/2007 | Van | |
| 7,497,851 B2 | 3/2009 | Koele | |
| 7,682,349 B2 | 3/2010 | Coenen | |
| 7,862,550 B2 | 1/2011 | Koele | |
| 7,901,393 B2 | 3/2011 | Matsuda | |
| 8,007,485 B2 | 8/2011 | Coenen | |
| 8,361,048 B2 | 1/2013 | Kuen | |
| 8,372,052 B2 | 2/2013 | Coenen | |
| 8,579,876 B2 | 11/2013 | Coenen | |
| 8,747,379 B2 | 6/2014 | Fletcher | |
| 9,421,137 B2 | 8/2016 | Lavon | |
| 9,498,389 B2 | 11/2016 | Trennepohl | |
| 2003/0130635 A1 | 7/2003 | Tate | |
| 2003/0206943 A1* | 11/2003 | Hammons | A61F 13/51305 424/443 |
| 2004/0102752 A1 | 5/2004 | Chen et al. | |
| 2007/0219521 A1 | 9/2007 | Hird | |
| 2011/0106035 A1* | 5/2011 | Arora | A61F 13/15203 604/367 |
| 2011/0139657 A1 | 6/2011 | Hird | |
| 2011/0139658 A1 | 6/2011 | Hird | |
| 2011/0139659 A1 | 6/2011 | Hird | |
| 2011/0139662 A1 | 6/2011 | Hird | |
| 2011/0152812 A1 | 6/2011 | Hird | |
| 2013/0006209 A1* | 1/2013 | Ruiz | A61F 13/68 604/385.14 |
| 2013/0197462 A1 | 8/2013 | Abuto et al. | |
| 2013/0211363 A1 | 8/2013 | Lavon | |
| 2014/0005020 A1 | 1/2014 | Lavon | |
| 2015/0265475 A1 | 9/2015 | Joseph et al. | |
| 2019/0000689 A1 | 1/2019 | Aviles et al. | |
| 2019/0117473 A1 | 4/2019 | Rosati et al. | |
| 2019/0314218 A1 | 10/2019 | Arora et al. | |
| 2019/0358140 A1* | 11/2019 | Huang | A61K 8/35 |

FOREIGN PATENT DOCUMENTS

| | | |
|---|---|---|
| CN | 102065911 A | 5/2011 |
| CN | 103282060 A | 9/2013 |
| CN | 106102680 A | 11/2016 |
| CN | 108291360 A | 7/2018 |
| WO | 2019168531 A1 | 9/2019 |

OTHER PUBLICATIONS

PCT Suppl. Search Report and Written Opinion for PCT/CN2020/072758 dated May 13, 2022, 9 pages.

PCT Search Report and Written Opinion for PCT/CN2020/072758 dated Oct. 26, 2020.

* cited by examiner

ABSORBENT ARTICLES COMPRISING SEMI-HYDROPHILIC COMPOSITIONS

CROSS REFERENCE TO RELATED APPLICATION

This application is a continuation of, and claims priority under 35 U.S.C. § 120 to, Patent Application No. PCT CN2020/072758, filed Jan. 17, 2020, the entire disclosure of which is hereby incorporated by reference.

FIELD

The present disclosure is generally directed to absorbent articles comprising topsheets comprising natural fibers and semi-hydrophilic compositions. The topsheets of the present disclosure may demonstrate acceptable fluid handling properties, especially for topsheets comprising natural fibers.

BACKGROUND

Nonwoven webs are useful in many fields, such as the medical field, the dusting and cleaning implement field, and the hygiene field, for example. In the hygiene field, absorbent articles, such as diapers, training pants, sanitary napkins, and adult incontinence products, may be used to absorb and contain urine, bowel movements, and/or menses (together "bodily exudates"). These absorbent articles may comprise nonwoven webs as various components thereof, such as topsheets, for example.

Nonwoven webs may comprise a variety of fiber types, including, for example, synthetic fibers such as polyethylene, polypropylene, and mixtures thereof. Recently, there has been an increased interest in supplementing or substituting synthetic components of nonwoven webs with naturally-derived components. For example, natural fibers, such as plant-based fibers, may be mixed with synthetic fibers, or may take the place of synthetic fibers, in nonwoven webs. Absorbent articles comprising nonwoven webs comprising natural fibers may be perceived by consumers as being of higher quality, more environmentally friendly, and/or softer against the skin of the wearer when utilized in a topsheet, an outer cover, or other context. Natural fibers, such as cotton, for example, may exhibit an increased tendency to form hydrogen bonds with polar fluids as compared to synthetic fibers. Polar fluids, such as urine and menses, may come into contact with and/or enter a topsheet comprising natural fibers. Instead of passing through the nonwoven topsheet and into a hydrophilic acquisition layer and/or an absorbent core, however, the polar fluids may form hydrogen bonds with at least some of the natural fibers, thus swelling the natural fibers and trapping fluid in or on the nonwoven topsheet. Capillary forces relied on to draw fluids from the nonwoven topsheet and into the hydrophilic acquisition layer and/or absorbent core may not be strong enough to overcome the hydrogen bonds formed between the polar fluids and natural fibers of the nonwoven topsheet. This swelling of the natural fibers may be undesirable because the polar fluids may remain in and/or on the topsheet and proximate to and/or in contact with the skin of the wearer, which is not consumer desired.

In some instances, nonwoven topsheets comprising natural fibers may be chemically treated to make the topsheet hydrophobic, more hydrophobic, or less hydrophilic, and thus at least inhibit polar fluids from bonding with the natural fibers of the nonwoven topsheet. Nonwoven topsheets may be coated with, for example, silicone, fluoride, or polymers to make the nonwoven topsheet hydrophobic, more hydrophobic, or less hydrophilic. While these coating processes may result in a topsheet that reduces or prevents polar fluids from bonding with the natural fibers of the topsheet, the resulting topsheet may also have significantly increased fluid strike-through time—the time it takes a fluid to traverse through a nonwoven topsheet—resulting in topsheets that may be slow to remove polar fluids from the surface of the skin of the wearer, leaving skin wet, which is not desired. Increased fluid strike-through times, therefore, are not desired. As such, nonwoven webs comprising natural fibers should be improved, especially in the nonwoven topsheet context.

SUMMARY

Aspects of the present disclosure solve some or all of the problems discussed above by providing an absorbent article comprising a liquid permeable topsheet comprising natural fibers, wherein the topsheet may comprise a semi-hydrophilic composition. The semi-hydrophilic composition may comprise a wax ester and a polyglyceryl emulsifier. The semi-hydrophilic wax composition may be disposed on a first side and/or a second side of the topsheet. The semi-hydrophilic wax composition may also be disposed throughout the topsheet, including on the natural fibers intermediate the first side and the second side. The semi-hydrophilic wax composition may also, or alternatively, be disposed on at least a portion of the surfaces of the natural fibers of the nonwoven topsheet and may form a coating on the surfaces of the natural fibers of the nonwoven topsheet. The semi-hydrophilic wax composition may render the nonwoven topsheet more permeable to polar fluids while preventing, or at least inhibiting, swelling of at least a portion of the nonwoven topsheet fibers. Stated another way, the semi-hydrophilic wax composition may at least inhibit the natural fibers from absorbing the polar fluids, thereby making the topsheets more permeable to the polar fluids. The topsheets of the present disclosure may be apertured to promote faster polar fluid penetration.

The present disclosure provides, in part, an absorbent article comprising a liquid permeable nonwoven topsheet comprising natural fibers, wherein the nonwoven topsheet may comprise a semi-hydrophilic composition comprising a wax ester and a polyglyceryl emulsifier, wherein a weight ratio of the wax ester to the polyglyceryl emulsifier is between about 1.5:1 and about 0.5:1, or between about 1.25:1 and about 0.75:1. The liquid permeable nonwoven topsheet may have a Contact Angle of less than about 100°, according to the Contact Angle Test disclosed herein. The liquid permeable nonwoven topsheet may have a Fluid Strike-Through time of between about 0.5 seconds to about 18 seconds, between about 0.5 seconds and about 12 seconds, or between about 1 second and about 5 seconds, according to the Fluid Strike-Through Test disclosed herein. The liquid permeable nonwoven topsheet may have a Rewet value of between about 1 mg and about 100 mg, between about 5 mg and about 85 mg, or between about 5 mg and about 60 mg, according to the Rewet Test disclosed herein.

The present disclosure provides, in part, an absorbent article comprising a liquid permeable nonwoven topsheet comprising natural fibers, wherein the nonwoven topsheet may comprise a semi-hydrophilic composition comprising a wax ester and a polyglyceryl emulsifier. The semi-hydrophilic wax composition may be disposed on a first side and a second side of the nonwoven topsheet by a process comprising the steps of: 1) melting the semi-hydrophilic wax composition; 2) dispersing the semi-hydrophilic wax composition in a continuous phase to form droplets of the semi-hydrophilic wax composition with a mean droplet size of less than 10 microns; 3) exposing the nonwoven topsheet to the melted semi-hydrophilic wax composition dispersion and 4) drying the nonwoven topsheet.

The present disclosure provides, in part, an absorbent article comprising a liquid permeable nonwoven topsheet comprising natural fibers, wherein the nonwoven topsheet may comprise a semi-hydrophilic composition, and wherein the nonwoven topsheet may have a Fluid Strike-Through time of between about 0.5 seconds to about 18 seconds, preferably between about 0.5 seconds and about 12 seconds, and more preferably between about 1 second and about 5 seconds, according to the Fluid Strike-Through Test. The nonwoven topsheet may have a Wicking Height of between about 0 mm and about 10 mm, between about 1 mm and about 8 mm, or between about 1 mm and about 7 mm, according to the Topsheet Wicking Test disclosed herein.

BRIEF DESCRIPTION OF THE DRAWINGS

The above-mentioned and other features and advantages of the present disclosure, and the manner of attaining them, will become more apparent, and the disclosure itself will be better understood, by reference to the following description of example forms of the disclosure taken in conjunction with the accompanying drawings, wherein.

DETAILED DESCRIPTION

Figure 1:
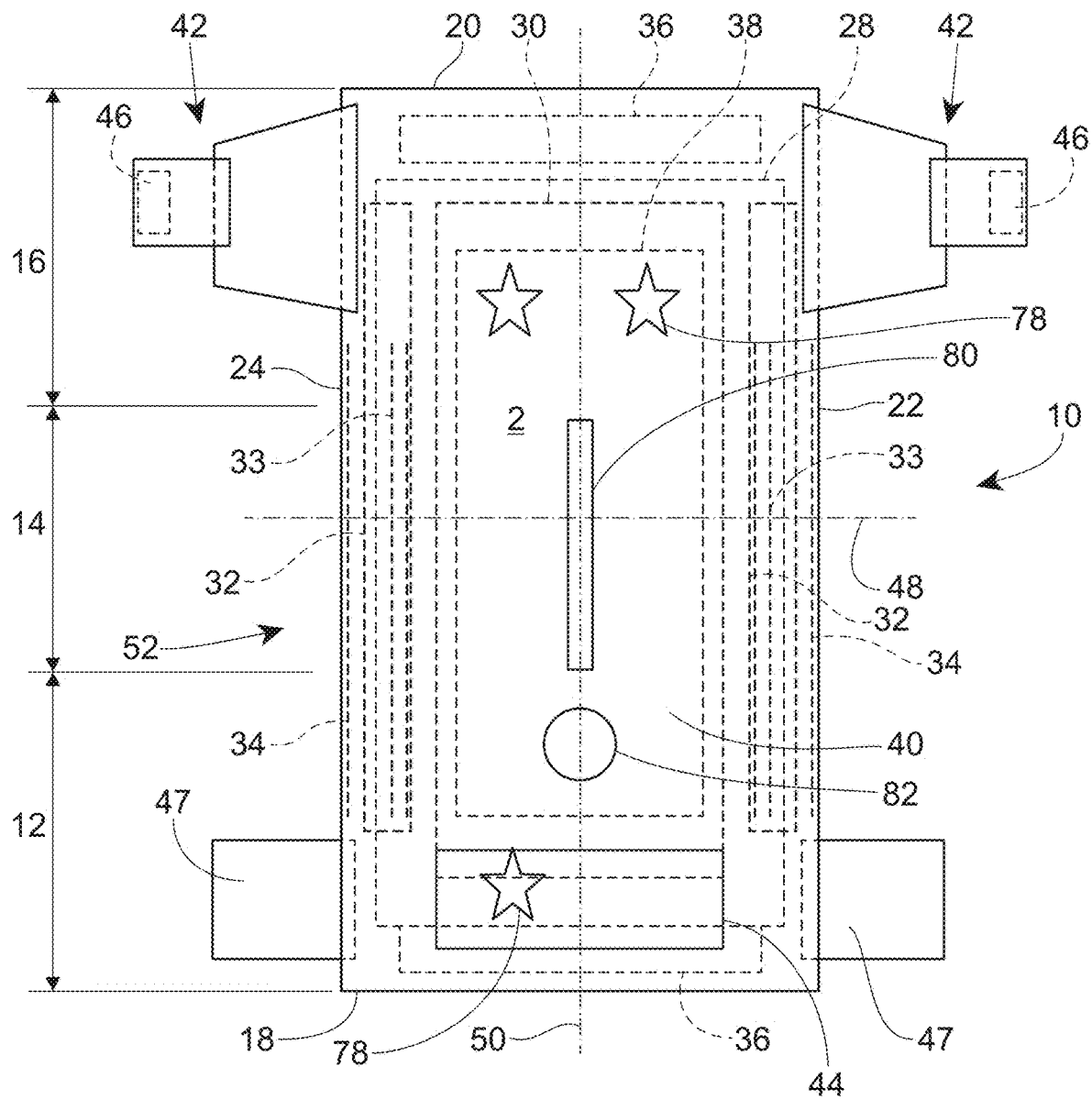
FIG. 1 is a plan view of an example absorbent article in the form of a taped diaper, garment-facing surface facing the viewer, in a flat laid-out state.

Various non-limiting forms of the present disclosure will now be described to provide an overall understanding of the principles of the structure, function, manufacture, and use of the absorbent articles comprising semi-hydrophilic compositions disclosed herein. One or more examples of these non-limiting forms are illustrated in the accompanying drawings. Those of ordinary skill in the art will understand that the absorbent articles comprising semi-hydrophilic compositions described herein and illustrated in the accompanying drawings are non-limiting example forms. The features illustrated or described in connection with one non-limiting form may be combined with the features of other non-limiting forms. Such modifications and variations are intended to be included within the scope of the present disclosure.

As used herein, the term "natural fibers" refers to elongated substances produced by plants and/or animals and comprises animal-based fibers and/or plant-based fibers. Natural fibers may comprise fibers harvested without any post-harvest treatment step as well as those having received a post-treatment step, such as, for example, washing, scouring, and bleaching. One example of natural fibers is cotton fibers.

As used herein, the terms "hydrophilic" and "hydrophobic" have meanings that are well established in the art with respect to the Contact Angle of water on the surface of a material. Thus, a material having a water Contact Angle of greater than about 90 degrees is considered hydrophobic, and a material having a water Contact Angle of less than about 90 degrees is considered hydrophilic. Compositions which are hydrophobic may increase the Contact Angle of water on the surface of a material, while compositions which are hydrophilic may decrease the Contact Angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case, neither the composition nor the material may be hydrophobic; however, the Contact Angle exhibited by the composition may be greater than that of the material. As another example, a composition may be more hydrophilic than a material. In such a case, neither the composition nor the material may be hydrophilic; however, the Contact Angle exhibited by the composition may be less than that exhibited by the material.

As used herein, the term "semi-hydrophilic" refers to a material having a water Contact Angle of between about 35° and about 100°, or between about 45° and about 98°, or between about 500 and about 95°, according to the Contact Angle Test disclosed herein. Thus, "semi-hydrophilic" spans a range that is mostly hydrophilic but may be slightly hydrophobic. As discussed further herein, it is believed that a nonwoven topsheet comprising a semi-hydrophilic composition and having a Contact Angle of between about 35 and about 100°, or between about 45 and about 98°, or between about 500 and about 95°, may facilitate the rapid transfer of polar fluids from a wearer-facing surface of a topsheet to an underlying acquisition layer and/or absorbent core. It is further believed that a topsheet having a Contact Angle lower than about 35 may interfere with the capillary action that may draw polar fluids into the underlying acquisition layer and/or absorbent core, and thus may result in polar fluids remaining within the topsheet. It is also believed that a topsheet having a Contact Angle higher than about 100 may interfere with polar fluid penetration through the topsheet.

General Description of an Absorbent Article

Figure 2:
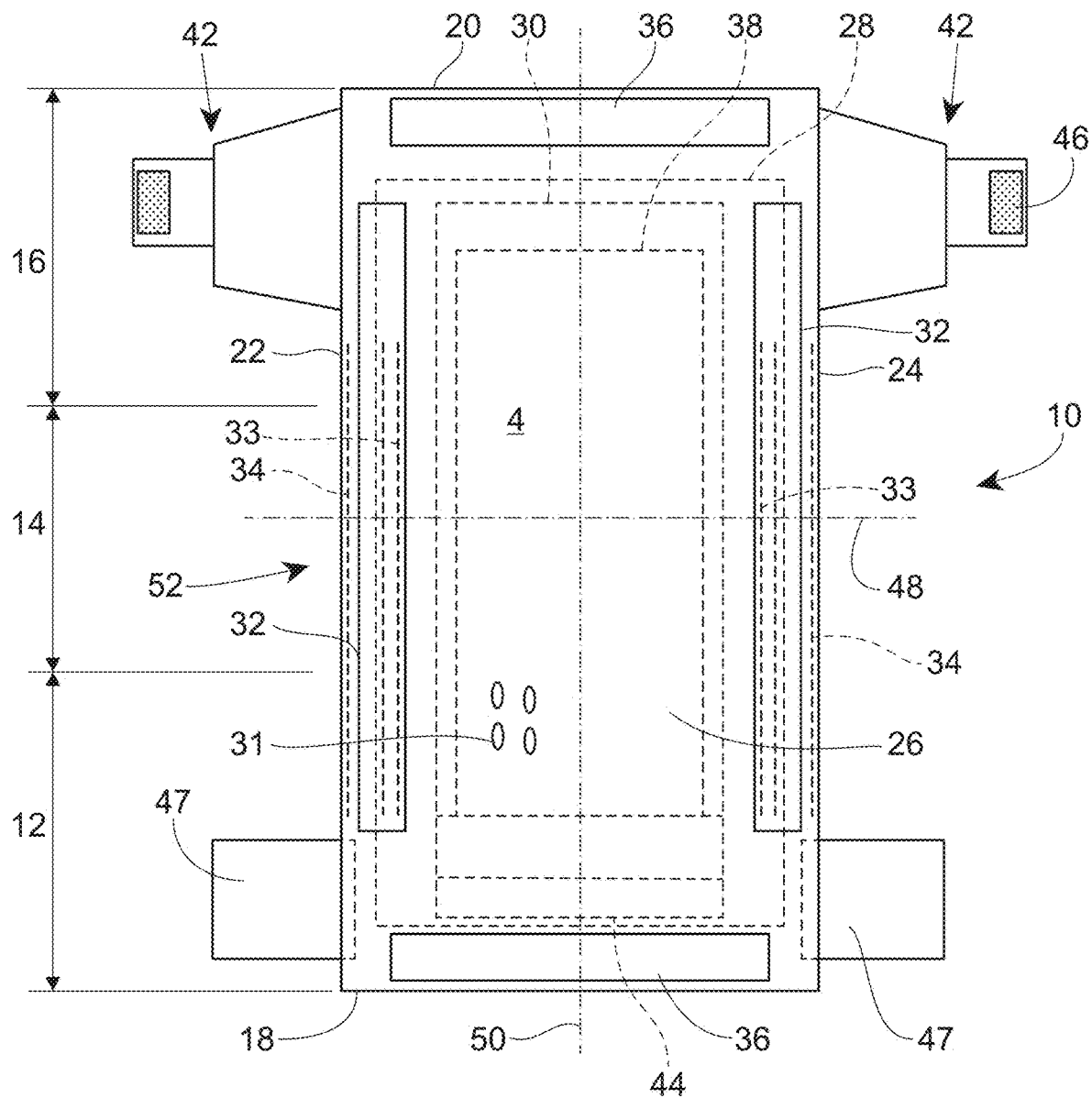
FIG. 2 is a plan view of the example absorbent article of FIG. 1, wearer-facing surface facing the viewer, in a flat laid-out state.
Figure 3:
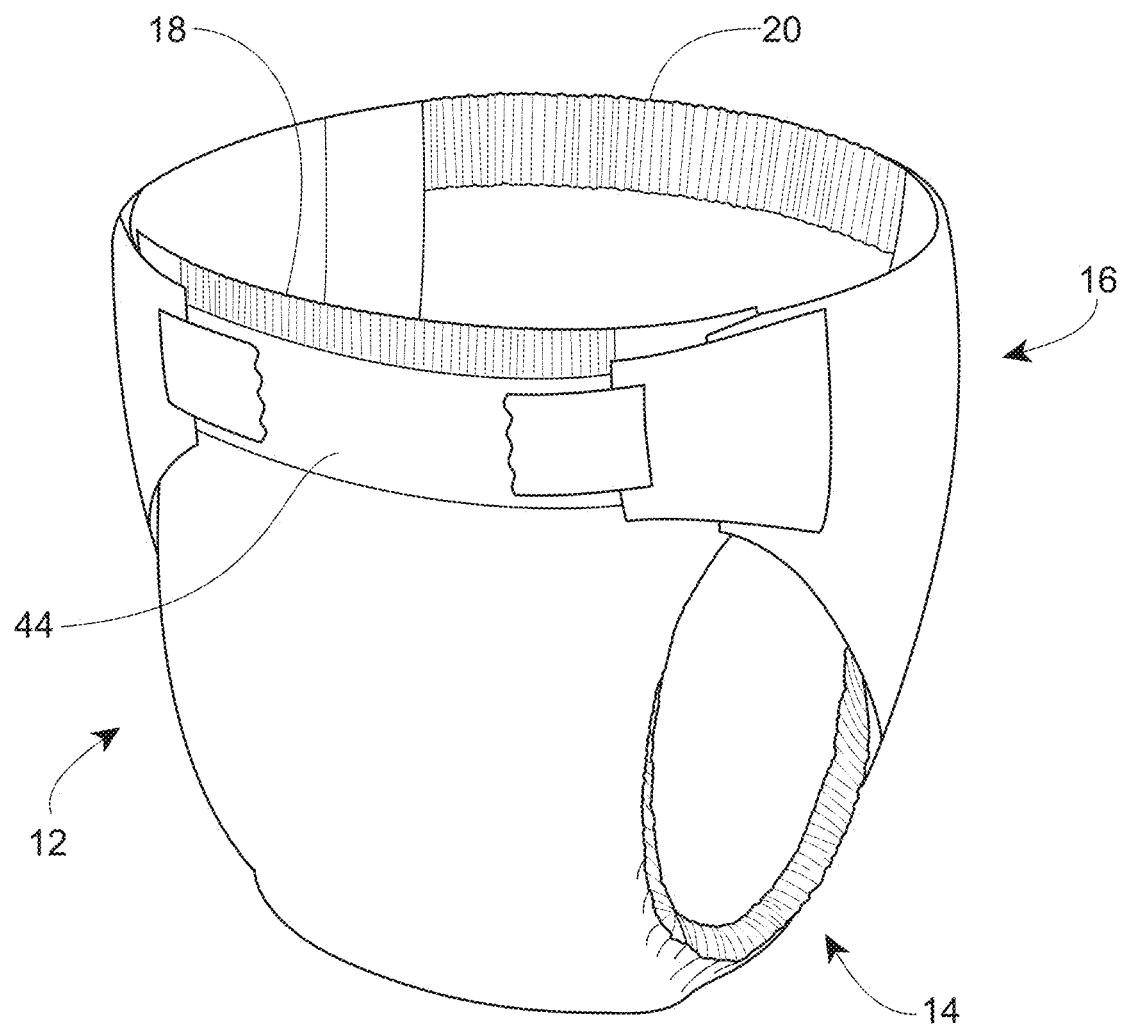
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be about ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
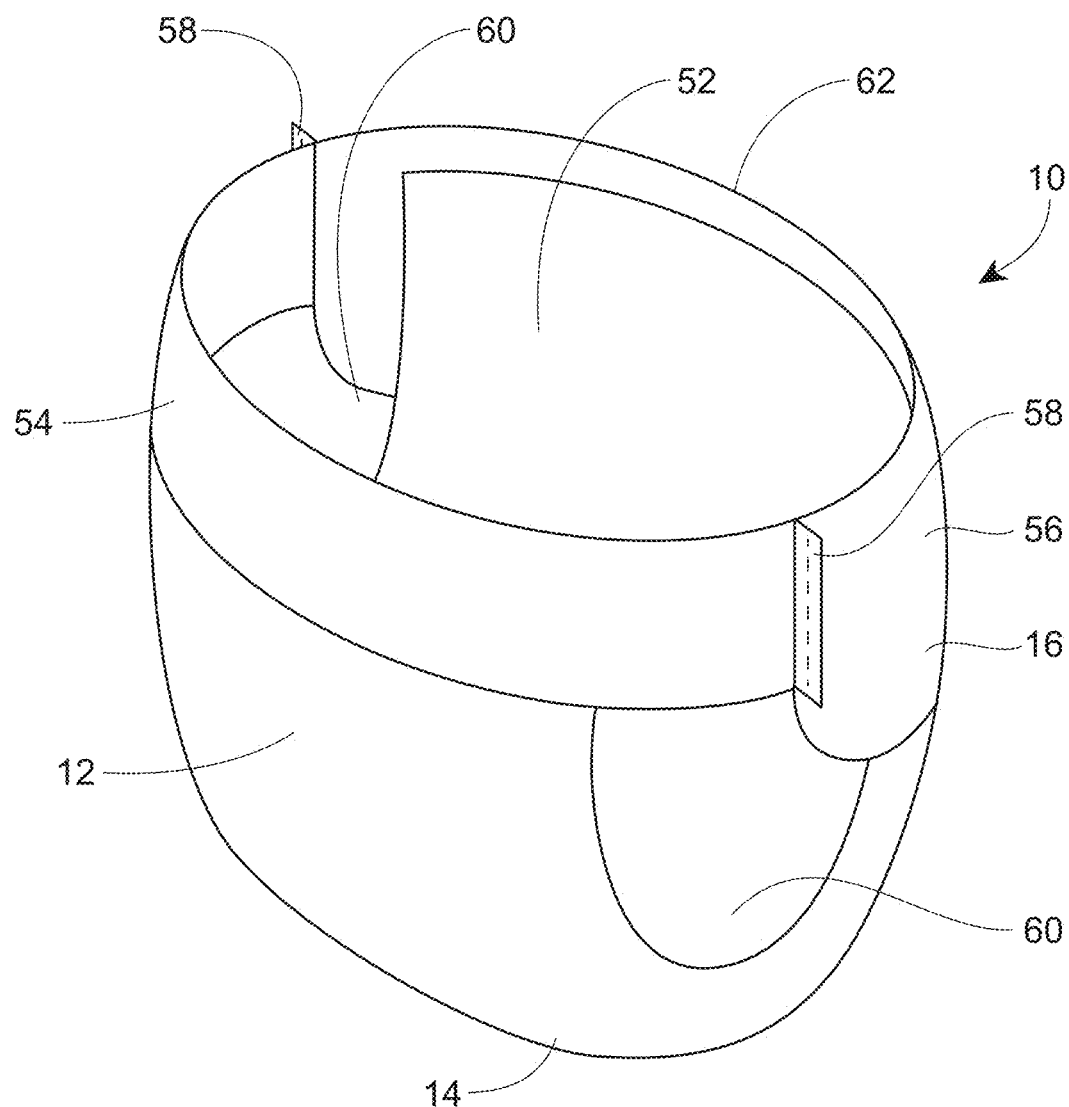
FIG. 4 is a front perspective view of an absorbent article in the form of a pant.
Figure 5:
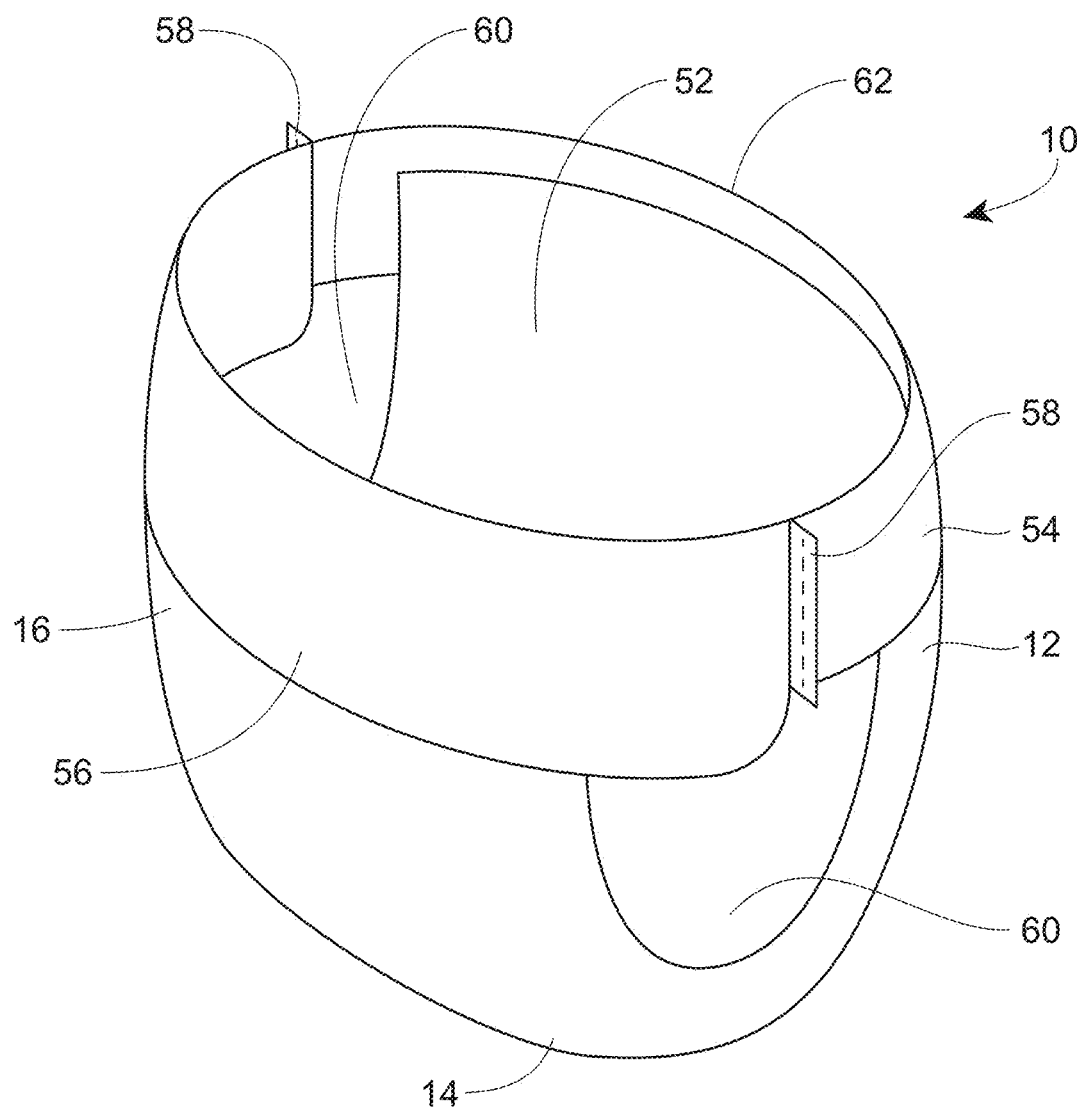
FIG. 5 is a rear perspective view of the absorbent article of FIG. 4.
Figure 6:
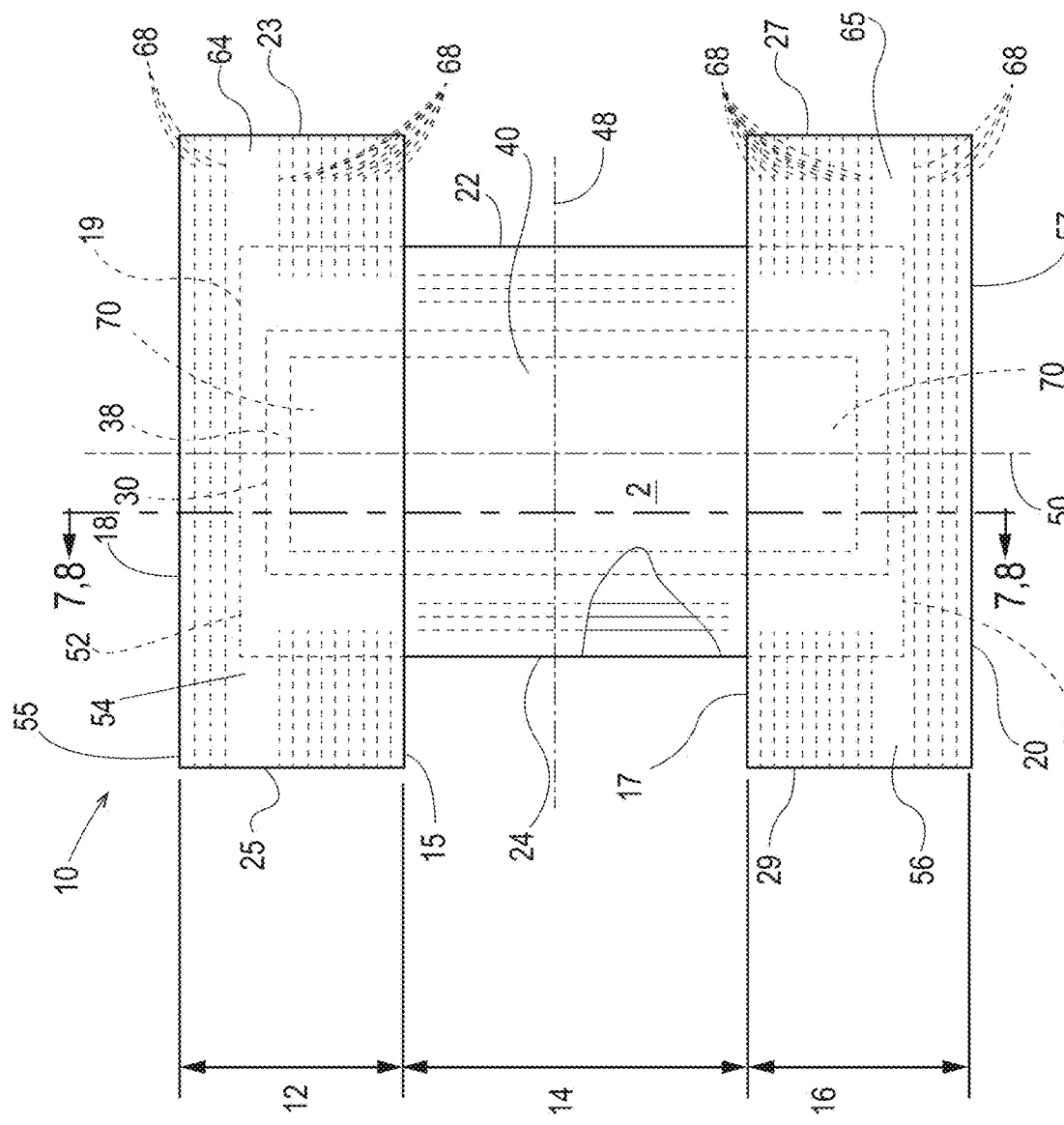
FIG. 6 is a plan view of the absorbent article of FIG. 4, laid flat, with a garment-facing surface facing the viewer.
Figure 7:
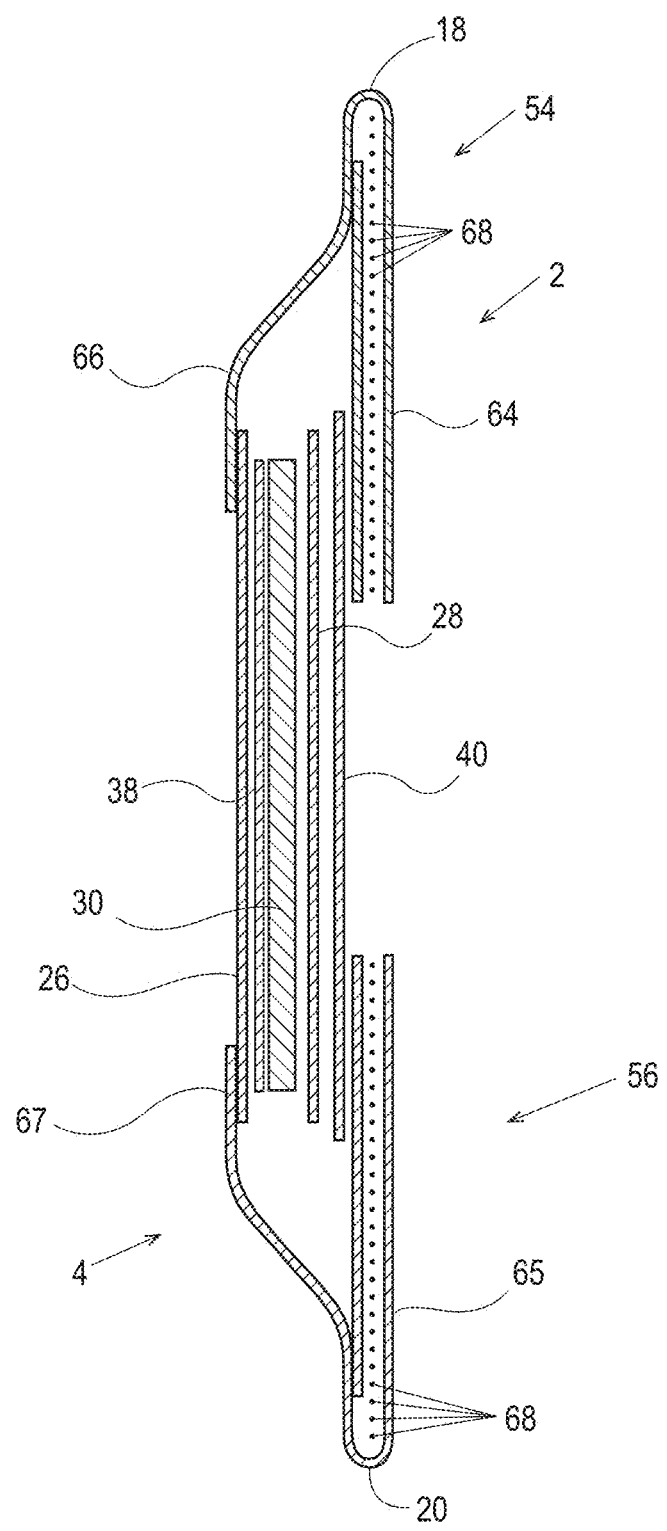
FIG. 7 is a cross-sectional view of the absorbent article taken about line 77 of FIG. 6.
Figure 8:
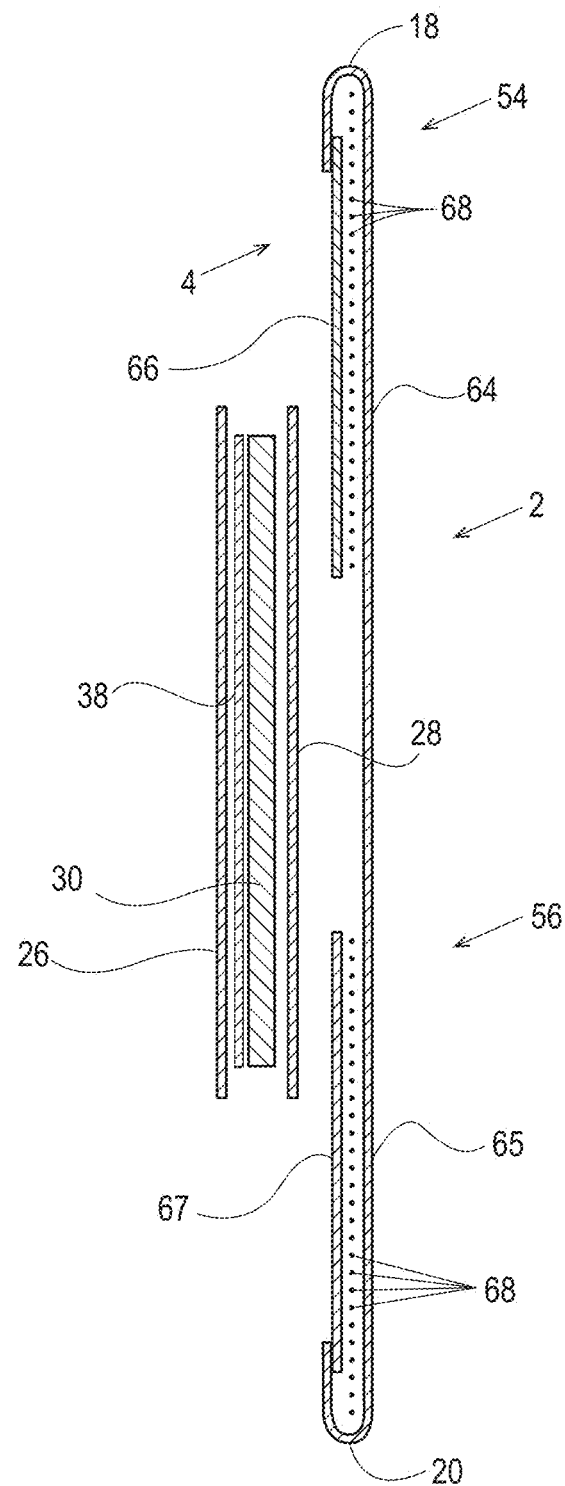
FIG. 8 is a cross-sectional view of the absorbent article taken about line 88 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 77 of FIG. 6. FIG. 8 is an example cross-sectional view of the absorbent article taken about line 88 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be about ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus.

The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is a part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. The topsheet may comprise one layer or more than one layer. The topsheet may be apertured (FIG. 2, element 31), may have any suitable three-dimensional features, and/or may have a plurality of embossments (e.g., a bond pattern).

The topsheet may comprise nonwoven web materials. Nonlimiting examples of nonwoven web materials that may be suitable for use as a topsheet include fibrous materials made from natural fibers, modified natural fibers, synthetic fibers, mixtures of natural and/or modified natural fibers with synthetic fibers, and/or combinations thereof. The nonwoven web materials may include, consist essentially of, or consist entirely of cellulosic plant fibers such as, for example, fibers from cotton, flax, hemp, jute, or mixtures thereof. In other examples, semi-synthetic fibers derived from cellulosic material, such as rayon (including viscose, lyocell, MODAL (a product of Lenzing AG, Lenzing, Austria) and cuprammonium rayon) may be used. The fibers comprising the nonwoven web materials may be processed to be suitably soft-feeling against the skin. Natural fibers may be consumer-preferred to appeal to a desire for natural and/or environmentally friendly products. The topsheet may comprise between about 20% and about 100%, between about 50% and about 100%, or between about 65% and 100%, by weight of the nonwoven topsheet of the natural fibers. In one example, the topsheet may comprise about 50% natural fibers and about 50% synthetic fibers. In another example, the topsheet may comprise about 20% natural fibers and about 80% synthetic fibers. In yet another example, the topsheet may comprise about 100% natural fibers, such as about 100% cotton fibers.

As discussed above, the topsheet may comprise a nonwoven web. The nonwoven web may be formed by any suitable process in which fibers may be distributed and accumulated onto a forming belt to form a batt having a desired distribution of fibers and/or a desired basis weight. Suitable processes may include, for example, carding, airlaying, and wetlaying. In another example, the nonwoven web may be formed by a co-forming process in which natural fibers of finite lengths are blended or mixed with streams of polymeric resin-based spun fibers of generally longer length than the natural fibers, and laid down on a forming belt to form a web. The web may be processed to consolidate the fibers and entangle them in the z-direction by processes that may include, for example, calendaring, needle punching, and hydroentanglement with water jets (also known as spunlace).

Further details regarding the nonwoven webs of the present disclosure used as topsheets are discussed herein.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features. The nonwoven webs of the present disclosure may be used as outer cover materials.

Absorbent Core

Figure 9:
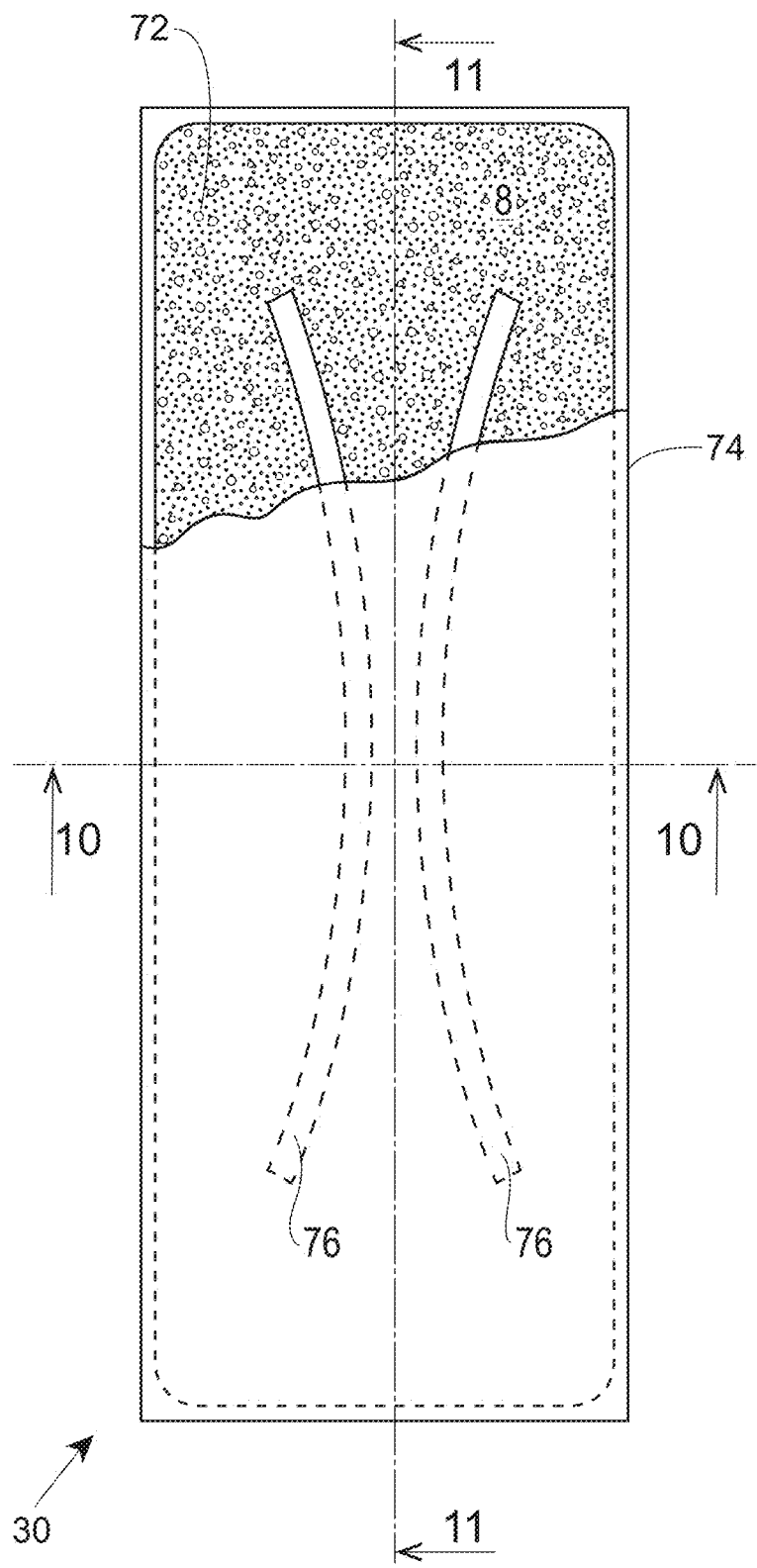
FIG. 9 is a plan view of an example absorbent core or an absorbent article.
Figure 10:
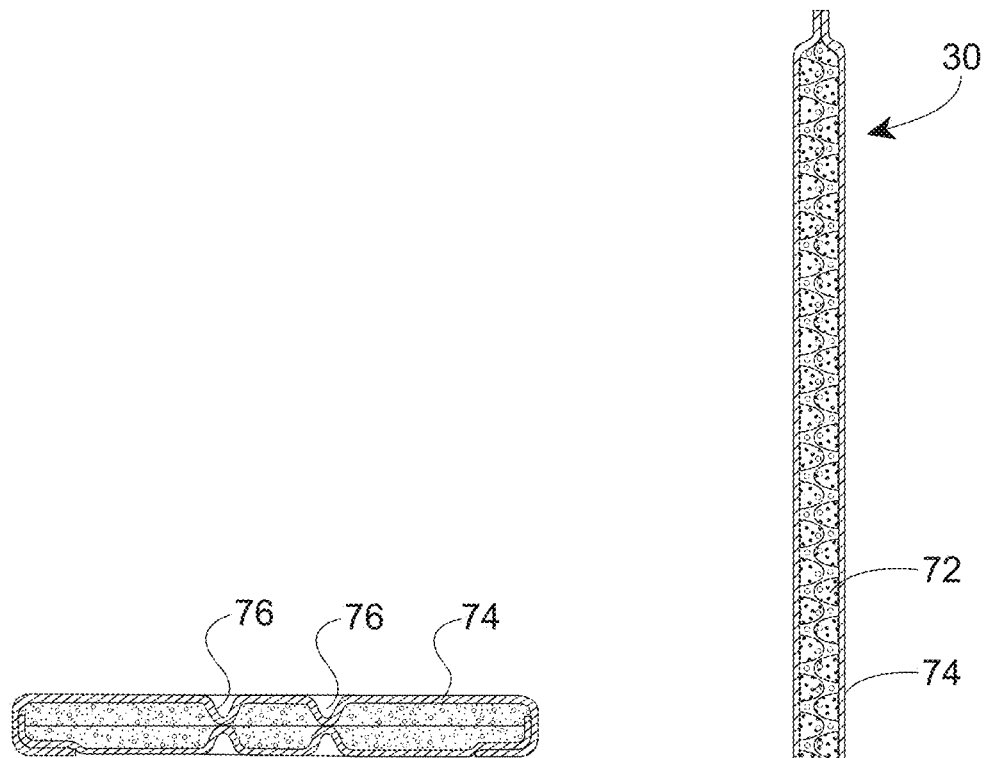
FIG. 10 is a cross-sectional view, taken about line 10-10, of the absorbent core of FIG. 9.
Figure 11:
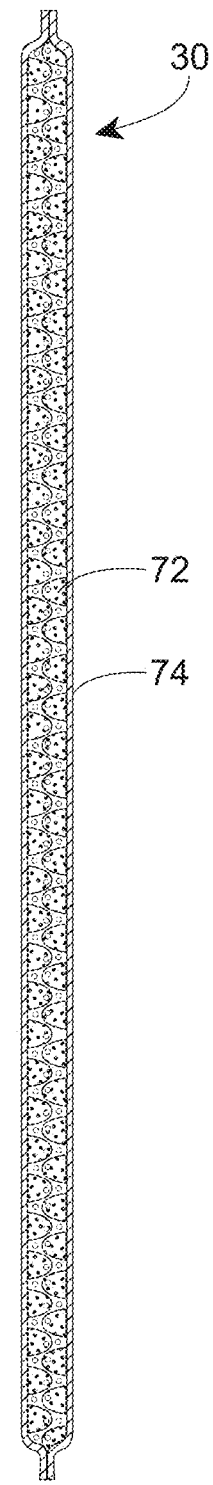
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, absorbent material). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Sanitary Napkin

Figure 12:
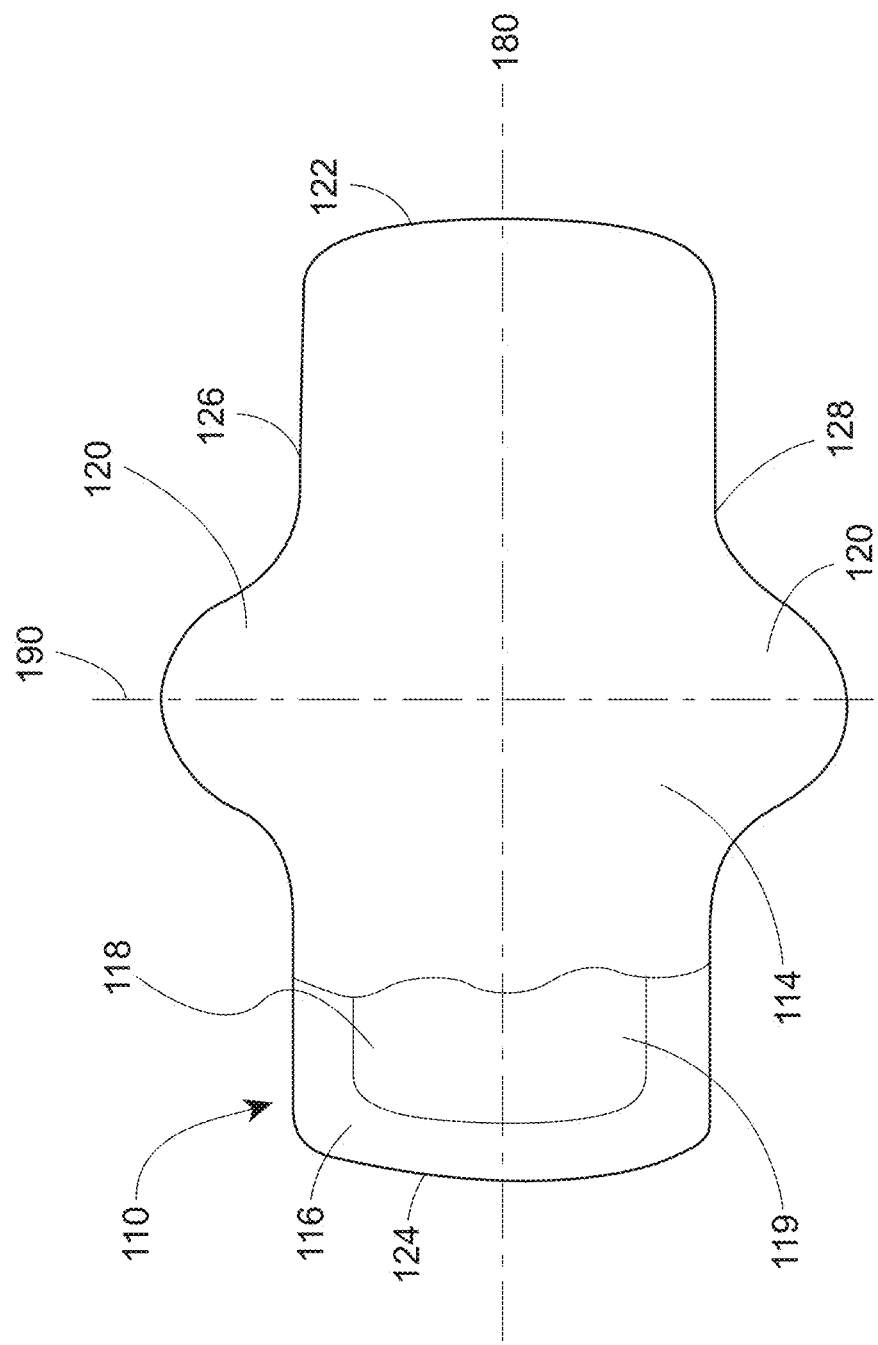
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. The semi-hydrophilic compositions disclosed herein may be used on topsheets of sanitary napkins to achieve the same benefits discussed herein. These topsheets may comprise natural fibers, such as cotton fibers, or may comprise mixtures of natural and synthetic fibers as disclosed herein. In some instances, the topsheets may comprise 100% cotton fibers.

Semi-Hydrophilic Composition/Natural Fibers

The absorbent articles of the present disclosure may comprise a liquid permeable nonwoven topsheet comprising natural fibers and one or more semi-hydrophilic compositions. The topsheets may comprise synthetic fibers in addition to the natural fibers. As discussed above, it may be desirable that liquid bodily exudates (e.g., urine) that contact a body-facing surface of the topsheet be moved quickly and completely, or nearly completely, away from the body of the wearer and be sequestered in underlying acquisition materials and/or an absorbent core. Generally, a liquid bodily exudate, which may be polar, may be drawn from the topsheet to the underlying acquisition materials and/or absorbent core by capillary action, due to a hydrophobicity gradient, thereby drawing the liquid bodily exudate away from generally less hydrophilic body-facing surfaces and into generally more hydrophilic underlying acquisition materials and/or absorbent core.

Natural fibers, such as, for example, cotton fibers, may be naturally hydrophobic due to the presence of naturally occurring waxy and oily compounds on the surface of the fibers. After ginning to separate the natural fibers from other plant materials, such as seeds, the raw fiber material may include substantial quantities of impurities (particulates, bits of plant matter, etc.) trapped within the fibrous matrices and/or adhered to the waxes and oils. These impurities may both discolor the fibers and make the fibers unsuitable or undesirable for many uses. In order to make raw natural fibers commercially acceptable for most uses, the fibers may first be processed in several steps to remove the impurities. Such processes, however, may also remove the natural waxes and oils and render the natural fiber more hydrophilic. Processed, natural fibers may exhibit an increased tendency to form hydrogen bonds with polar liquid bodily exudates, such as urine, for example. Polar fluids may form strong hydrogen bonds with the processed hydrophilic natural fibers, which may cause the natural fibers to swell. The hydrogen bonds may be stronger than the capillary forces drawing polar fluids into the underlying acquisition layer and/or absorbent core of an absorbent article, thereby preventing, or at least inhibiting, the rapid transfer of the polar away from the body of the wearer in an absorbent article context.

In order to ensure that the polar fluid(s) contacting the wearer-facing surface of a topsheet of an absorbent article will move suitably rapidly via capillary action in a z-direction toward the garment-facing surface of the topsheet, where the polar fluids can be drawn into the underlying absorbent layer(s), a semi-hydrophilic composition may be applied to the topsheet. The semi-hydrophilic composition may reduce or prevent polar fluid contact with the natural fibers of the topsheet, while still allowing the polar fluid to pass through the fiber matrix of the topsheet. The semi-hydrophilic composition may be disposed on a portion of, or all of, the fibers of the topsheet and/or form a coating on the fibers, or portions of the fibers. In the case of a topsheet comprising multiple layers, the semi-hydrophilic composition may be disposed on a portion of, or all of, only one layer, for example only the wearer-facing layer, of the multi-layer topsheet. In other instances, two or more than two layers of a topsheet may comprise the semi-hydrophilic composition on all or portions thereof.

The semi-hydrophilic composition of the present disclosure may comprise a wax ester and a polyglyceryl emulsifier, wherein a weight ratio of the wax ester to the polyglyceryl ester may be between about 1.5:1 to about 0.5:1, or between about 1.25:1 to about 0.75:1. It is believed that the wax composition comprising the polyglyceryl emulsifier and the wax ester in a weight ratio of between about 1.5:1 and 0.5:1 and that is disposed on a portion of, or all of, the fibers of the topsheet may provide a surface on the fibers of the topsheet with a Contact Angle of between about 350 and about 100°, or between about 450 and about 98°, or between about 500 and about 95°, according to the Contact Angle Test disclosed herein. Without wishing to be bound by theory, it is believed that a coating applied to a nonwoven topsheet and resulting in the topsheet having a Contact Angle of between about 35 and about 100°, or between about 45 and about 98°, or between about 50 and about 95°, according to the Contact Angle test disclosed herein, may facilitate the rapid transfer of polar fluids from the wearer-facing surface of the topsheet to the underlying acquisition layer and/or absorbent core due to the relatively hydrophilic nature of the coating. It is further believed that a topsheet having a Contact Angle lower than about 35 may interfere with the capillary action drawing polar fluids into the underlying acquisition layer and/or absorbent core, and may result in polar fluids remaining within the topsheet. It is also believed that a topsheet having a Contact Angle higher than about 100 may interfere with polar fluid penetration through the topsheet.

The semi-hydrophilic composition of the present disclosure may be insoluble or at least not readily soluble in water or other polar fluids, including, for example, bodily exudates such as urine. The semi-hydrophilic composition may reduce or prevent fluid contact with the fibers comprising the topsheet by, for example, forming a physical barrier by coating at least a portion of, or all of, the fibers that comprise the topsheet. In instances where the topsheet comprises both natural and synthetic fibers, at least portions of, or all of, the natural fibers may be coated. In other instances, at least some of, or all of, both the natural and synthetic fibers may be coated. The semi-hydrophilic wax composition may have a Contact Angle of between about 35 and about 100°, or between about 450 and about 98°, or between about 50 and about 95°, thereby presenting a relatively hydrophilic surface that may allow polar fluids to readily pass by the fibers of the topsheet without the fluid coming into contact with the fibers. Therefore, the semi-hydrophilic wax composition may reduce or prevent hydrogen bonding between polar fluids and the topsheets comprising the natural fibers, while still allowing polar fluids to pass through the fiber matrix of the topsheet and into underlying layers.

As discussed above, the semi-hydrophilic composition of the present disclosure may comprise a wax ester. The wax ester may comprise an ester of a fatty acid and a fatty alcohol. The fatty acid component of the wax ester may be a long chain fatty acid or a very long chain fatty acid, comprising between about 14 to about 26 carbon atoms. The fatty alcohol of the wax ester may be a long chain or a very long chain fatty alcohol, comprising between about 14 to about 26 carbon atoms. The wax ester may have a molecular chain length of between about 28 and about 48 carbon atoms, or between about 36 and about 46, or between about 40 and about 44 carbon atoms. The wax ester may comprise saturated fatty acids and fatty alcohols, monounsaturated fatty acids and fatty alcohols, polyunsaturated fatty acids and fatty alcohols, and combinations thereof. The wax ester may have a degree of unsaturation. The degree of unsaturation of the wax ester may be measured by the Iodine Value Test, as disclosed herein. The wax ester may have an iodine value of between about 35 g/100 g and about 50 g/100 g, between about 38 g/100 g and about 48 g/100 g, or between about 40 g/100 g and about 44 g/100 g, according to the Iodine Value Test disclosed herein. Without wishing to be bound by theory, it is believed that a wax ester having a degree of unsaturation as described above may assist in the formation of a semi-hydrophilic wax composition that remains pliable upon application to a topsheet and/or to the fibers of a topsheet. Wax esters having an iodine value lower than that described above may tend to harden and become resistant to flexing or bending, which is not desirable. In the context of an absorbent article, such pliability may be beneficial because an absorbent article may be bent and flexed during the course of use and wear, requiring the wax composition to bend and flex along with the article. The application of a wax composition comprising a wax ester with a low iodine value (corresponding to a low degree of unsaturation) to the topsheet of an absorbent article may result in the wax composition cracking and flaking off of the topsheet during use. This may cause the natural fibers to be exposed to polar fluids and to swell when the polar fluids contact the natural fibers.

Figure 13:
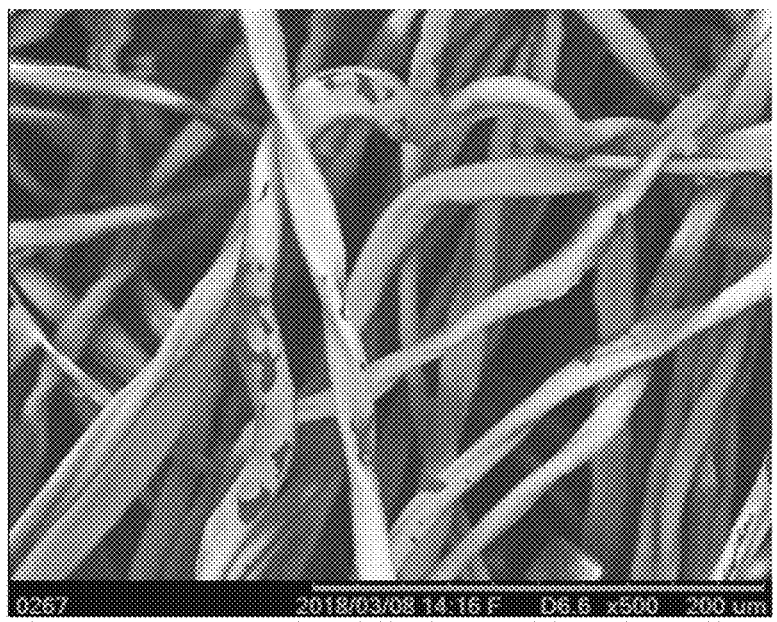
FIG. 13 is a scanning electron micrograph of a portion of a nonwoven topsheet comprising 100% cotton fibers and a wax composition with a low degree of unsaturation.

FIG. 13 is a scanning electron micrograph of a portion of a topsheet comprising 100% cotton fibers and a wax composition comprising saturated jojoba wax ester with an Iodine Value of less than 10 g/100 g. As shown in FIG. 13, the wax composition is cracked and is flaking off of the topsheet fibers. The wax ester may be interesterified or hydrogenated to provide a wax ester comprising the appropriate degree of unsaturation, as determined by the Iodine Value Test. While the wax composition of FIG. 13 has a low degree of unsaturation, the wax composition may still provide some benefits to the topsheets comprising natural fibers for fluid acquisition and fluid strike-through.

In one example, the wax ester may comprise a natural wax ester. A natural wax ester may be a wax ester derived from a plant or animal source, such as, for example, the leaves, fruit, seeds, or other parts of a plant. In one example, the wax ester may comprise jojoba wax ester, derived from any part of the jojoba plant (*Simmondsia chinensis*). In another example, the wax ester may comprise interesterified jojoba wax ester that has an iodine value of between about 35 g/100 g and about 50 g/100 g, according to the Iodine Value Test disclosed herein.

The semi-hydrophilic composition of the present disclosure may have a melting temperature of between about 35° C. and about 80° C., between about 45° C. and about 70° C., and between about 50° C. and about 60° C. A melting temperature of the semi-hydrophilic composition within this range may be beneficial to provide a pliable and flexible semi-hydrophilic composition, while remaining in a solid state at a body temperature of a wearer of the absorbent article. Providing a composition that has a melting temperature below or within the range of the body temperature of a wearer may cause the composition to melt during use and transfer from the absorbent article to the body of the wearer. This may result in undesirable residue on the skin of the wearer. Melting of the composition upon wear may also result in a reduction in its efficacy as a physical barrier against a polar fluid contacting the fibers of the topsheet.

As discussed above, the semi-hydrophilic composition of the present disclosure may comprise a polyglyceryl emulsifier. The molecular structure of the polyglyceryl emulsifier may comprise a polar head region and a non-polar or less polar chain. The polar head region of the polyglyceryl emulsifier may comprise glycerin, polyglycerins, and/or combinations thereof. The non-polar or less polar chain may comprise an aliphatic hydrocarbon chain. In one example, the polyglyceryl emulsifier comprises polyglyceryl-2 stearate.

Figure 14:
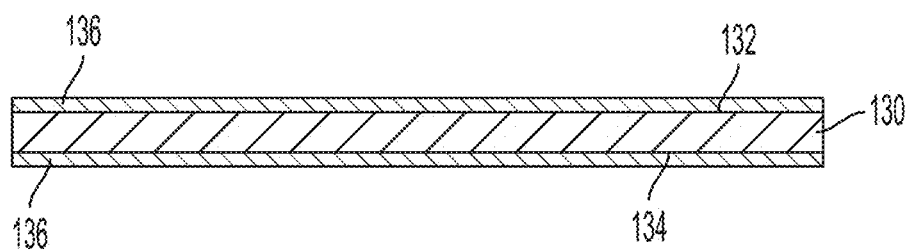
FIG. 14 is a schematic cross-sectional illustration of a portion of a nonwoven topsheet comprising a semi-hydrophilic composition disposed on a first side and a second side of the topsheet.

FIG. 14 is a schematic cross-sectional illustration of a portion of a topsheet of the present disclosure. A semi-hydrophilic composition 136 of the present disclosure may be disposed on a first side 132 and a second side 134 of a portion of a topsheet 130 comprising natural fibers. The semi-hydrophilic composition 136 may be disposed on a portion of, or all of, the fibers on the first side and the second side of the topsheet 130. The semi-hydrophilic composition 136 may form a coating on at least a portion of the fibers and may reduce or prevent polar fluids from contacting the fibers. The semi-hydrophilic composition may also be present between the first side 132 and the second side 134. The fibers may be or comprise natural fibers, such as cotton fibers.

Figure 15:
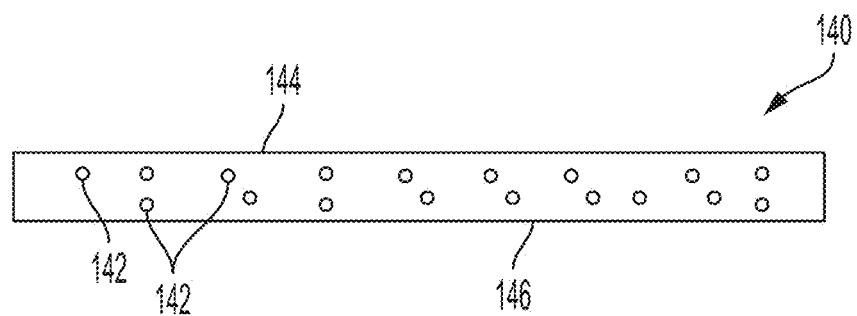
FIG. 15 is a schematic cross-sectional illustration of a portion of a nonwoven topsheet comprising a semi-hydrophilic composition disposed intermediate a first side and a second side of the topsheet.

FIG. 15 is a schematic cross-sectional illustration of a portion of a topsheet of the present disclosure. A semi-hydrophilic composition 142 of the present disclosure may be disposed between a first side 144 and a second side 146 of a portion of a topsheet 140. The semi-hydrophilic composition 142 may be disposed on fibers comprising the topsheet 140 that are disposed between the first side 144 and the second side 146 of the topsheet 140. The semi-hydrophilic composition 142 may be disposed on a portion of, or all of, the surfaces of fibers between the first side 144 and the second side 146 of the topsheet 140. The semi-hydrophilic composition 142 may form a coating on the fibers and may reduce or prevent polar fluids from contacting the fibers, while allowing the polar fluids to pass through the fiber matrix of the topsheet. A semi-hydrophilic composition of the present disclosure may be disposed on the surface of the natural fibers comprising a nonwoven topsheet. The semi-hydrophilic composition may also be present on the first side 144 and the second side 146. The fibers may be or comprise natural fibers, such as cotton fibers.

Figure 16:
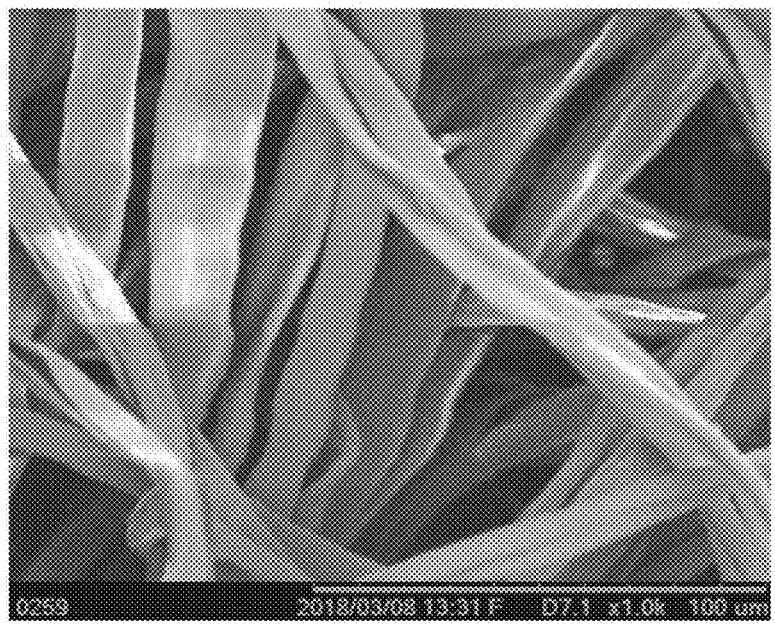
FIG. 16 is a scanning electron micrograph of a topsheet, wherein the fibers of the topsheet are at least partially coated by a semi-hydrophilic wax composition.

FIG. 16 is a scanning electron micrograph of a portion of a topsheet of the present disclosure, wherein the fibers of the topsheet are coated by a semi-hydrophilic wax composition. The semi-hydrophilic wax composition may be substantially free from cracks and flaking, and may provide a consistent coating over most of, or all of, the fibers of the topsheet. The fibers may be or comprise natural fibers, such as cotton fibers.

Figure 17:
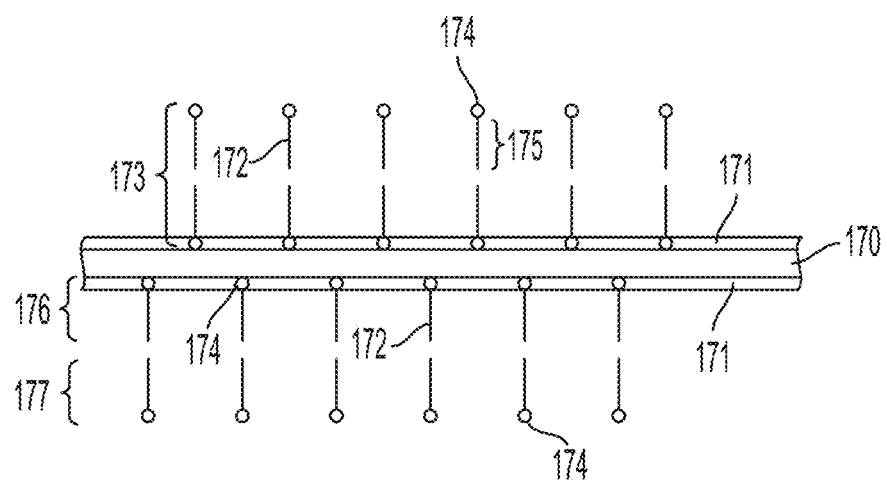
FIG. 17 is a schematic cross-sectional illustration of a portion of a topsheet comprising a semi-hydrophilic wax composition, wherein the semi-hydrophilic wax composition forms a bi-layer structure on the surface of the fibers of the topsheet.

As discussed above, the semi-hydrophilic wax composition may form a physical barrier around, or at least partially around, the fibers of the topsheet. The fibers may be or comprise natural fibers, such as cotton fibers. The components of the semi-hydrophilic wax composition may orient into a bi-layer structure. Referring to FIG. 17, it is believed that the wax ester component 171 of the semi-hydrophilic wax composition may form a physical barrier around the fibers 170 of the topsheet that may reduce or prevent contact between the fibers 170 of the topsheet and polar fluids, such as urine, that may pass through the topsheet. It is believed that the polyglyceryl emulsifier component 172 of the semi-hydrophilic wax composition may orient itself into a bilayer structure 173, wherein each layer of the bilayer structure comprises a polar head region (a high polarity portion) 174 and a non-polar or less-polar chain region (a low polarity portion) 175, wherein the polar head region 174 of a layer most proximal to the fibers 176 faces the fibers 170, and wherein the polar head region 174 of a layer most distal from the fibers 177 forms an outermost portion of the surface of the nonwoven topsheet. It is further believed that the rate of application of the semi-hydrophilic wax composition to the topsheet affects the molecular arrangement of the composition on the topsheet or on the fibers of the topsheet. The semi-hydrophilic wax composition may be applied to the topsheet at a rate of between about 0.5% and about 1.5%, or between about 0.75% and about 1.25%, by weight of the nonwoven topsheet, of the semi-hydrophilic wax composition.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages.

Bio-Based Content for Absorbent Article Components

Components of the disposable absorbent articles described in this specification can at least partially be comprised of bio-sourced content as described in U.S. Pat. Appl. Publ. No. 2007/0219521 A1 Hird et al., published on Sep. 20, 2007, U.S. Pat. Appl. Publ. No. 2011/0139658 A1 Hird et al., published on Jun. 16, 2011, U.S. Pat. Appl. Publ. No. 2011/0139657 A1 Hird et al., published on Jun. 16, 2011, U.S. Pat. Appl. Publ. No. 2011/0152812 A1 Hird et al., published on Jun. 23, 2011, U.S. Pat. Appl. Publ. No. 2011/0139662 A1 Hird et al., published on Jun. 16, 2011, and U.S. Pat. Appl. Publ. No. 2011/0139659 A1 Hird et al., published on Jun. 16, 2011. These components include, but are not limited to, backsheet films, backsheet nonwovens, side panel nonwovens, barrier leg cuff nonwovens, absorbent materials, nonwoven acquisition layers, core wrap nonwovens, adhesives, fastener hooks, and fastener landing zone nonwovens and film bases.

A disposable absorbent article component may comprise a bio-based content value from about 10% to about 100%, according to ASTM D6866-10, method B. In other forms, a disposable absorbent article component may comprise a bio-based content value from about 25% to about 75%, according to ASTM D6866-10, method B. Instill other forms, a disposable absorbent article component may comprise a bio-based content value from about 50% to about 60%, according to ASTM D6866-10, method B.

In order to apply the methodology of ASTM D6866-10, method B, to determine the bio-based content of any disposable absorbent article component, a representative sample of the disposable absorbent article component must be obtained for testing. The disposable absorbent article component may be ground into particulates less than about 20 mesh using known grinding methods (e.g., Wiley® mill), and a representative sample of suitable mass taken from the randomly mixed particles.

EXAMPLES

All examples described below comprising a coating composition were coated by the process described in the section entitled "Method of Manufacturing Topsheets Comprising a Semi-Hydrophilic Composition" herein. Comparative Examples 1-12 and Examples 1 and 8 were prepared on laboratory scale equipment. The analysis of all examples was performed following the Test Procedures disclosed herein.

Comparative Example 1

The nonwoven topsheet described herein as Comparative Example 1 is a nonwoven web comprising 100% cotton fibers. The fibers are formed into a nonwoven web by a spunlace process. The nonwoven topsheet has a basis weight of 35 gsm. No coating composition is provided.

Comparative Example 2

The nonwoven topsheet described herein as Comparative Example 2 is the nonwoven topsheet material of Comparative Example 1 and has a composition comprising rice bran wax at a level of 1.1% by weight of the topsheet.

Comparative Example 3

The nonwoven topsheet described herein as Comparative Example 3 is the nonwoven topsheet material of Comparative Example 1 and has a composition comprising beeswax at a level of 1.0% by weight of the topsheet.

Comparative Example 4

The nonwoven topsheet described herein as Comparative Example 4 is the nonwoven topsheet material of Comparative Example 1 and has a composition comprising hydrogenated olive oil at a level of 1.2% by weight of the topsheet.

Comparative Example 5

The nonwoven topsheet described herein as Comparative Example 5 is the nonwoven topsheet material of Comparative Example 1 and has a composition comprising candelilla wax at a level of 1.0% by weight of the topsheet.

Comparative Example 6

The nonwoven topsheet described herein as Comparative Example 6 is the nonwoven topsheet material of Comparative Example 1 and has a composition comprising vegetable wax at a level of 1.1% by weight of the topsheet.

Comparative Example 7

The nonwoven topsheet described herein as Comparative Example 7 is the nonwoven topsheet material of Comparative Example 1 and has a composition comprising paraffin wax at a level of 0.9% by weight of the topsheet.

Comparative Example 8

The nonwoven topsheet described herein as Comparative Example 8 is the nonwoven topsheet material of Comparative Example 1 and has a composition comprising jojoba wax at a level of 1.0% by weight of the topsheet.

Example 1

The nonwoven topsheet described herein as Example 1 is the nonwoven topsheet material of Comparative Example 1 and has a composition comprising a mixture of jojoba wax ester and polyglyceryl-2 stearate (PolyAquol™ W2, available from Innovacos Corp., Mt. Arlington, N.J.) at a level of 1.0% by weight of the topsheet. The jojoba wax ester is interesterified to achieve a melting point of 56° C.-60° C. (Tradename Floraester®-60, available from International Flora Technologies, Ltd., Chandler, Ariz.). The semi-hydrophilic wax composition comprises 1 part jojoba wax ester to 1 part polyglyceryl-2 stearate.

Example 2

The nonwoven topsheet described herein as Example 2 has the same materials and is prepared in the same manner as Example 1.

TABLE 1

Fluid performance data of nonwoven topsheets comprising coatings of various compositions.

| Example | Topsheet Material | Coating Material | Coating Level (% by wt. of topsheet) | Fluid Strike-Through (s) | Rewet (mg) |
|---|---|---|---|---|---|
| Comparative Example 1 | 35 gsm 100% cotton | None | 0 | 1.6 | 525.3 |
| | 35 gsm 100% cotton | None | 0 | 1.5 | 563.3 |
| Comparative Example 2 | 35 gsm 100% cotton | Rice Bran Wax | 1.1 | 740.9 | 72.0 |
| | 35 gsm 100% cotton | Rice Bran Wax | 1.1 | 891.0 | 112.0 |
| Comparative Example 3 | 35 gsm 100% cotton | Beeswax | 1.0 | 864.2 | 80.0 |
| | 35 gsm 100% cotton | Beeswax | 1.0 | 823.3 | 58.1 |
| Comparative Example 4 | 35 gsm 100% cotton | Hydrogenated Olive Oil | 1.2 | 606.0 | 39.4 |
| | 35 gsm 100% cotton | Hydrogenated Olive Oil | 1.2 | 728.5 | 41.2 |

TABLE 1-continued

Fluid performance data of nonwoven topsheets comprising coatings of various compositions.

| Example | Topsheet Material | Coating Material | Coating Level (% by wt. of topsheet) | Fluid Strike-Through (s) | Rewet (mg) |
|---|---|---|---|---|---|
| Comparative Example 5 | 35 gsm 100% cotton | Candelilla Wax | 1.0 | 651.9 | 37.4 |
| | 35 gsm 100% cotton | Candelilla Wax | 1.0 | 691.1 | 38.8 |
| Comparative Example 6 | 35 gsm 100% cotton | Vegetable Wax | 1.1 | 110.9 | 49.4 |
| | 35 gsm 100% cotton | Vegetable Wax | 1.1 | 198.2 | 39.8 |
| Comparative Example 7 | 35 gsm 100% cotton | Paraffin Wax | 0.9 | 394.2 | 48.9 |
| | 35 gsm 100% cotton | Paraffin Wax | 0.9 | 442.3 | 43.7 |
| Comparative Example 8 | 35 gsm 100% cotton | Jojoba Wax | 1.0 | 403.3 | 68.9 |
| | 35 gsm 100% cotton | Jojoba Wax | 1.0 | 372.2 | 77.8 |
| Example 1 | 35 gsm 100% cotton | Jojoba wax ester/ polyglyceryl-2 stearate (1:1) | 1.0 | 8.2 | 39.6 |
| | 35 gsm 100% cotton | Jojoba wax ester/ polyglyceryl-2 stearate (1:1) | 1.0 | 5.3 | 45.5 |
| Example 2 | 35 gsm 100% cotton | Jojoba wax ester/ polyglyceryl-2 stearate (1:1) | 1.0 | 7.8 | 58 |
| | 35 gsm 100% cotton | Jojoba wax ester/ polyglyceryl-2 stearate (1:1) | 1.0 | 6.2 | 40.1 |

As shown in TABLE 1 above, all samples were tested for Fluid Strike-Through Time and Rewet in duplicate. Test procedures for the Fluid Strike-Through Test and the Rewet Test can be found under the Test Procedures section herein. As discussed further in the Test Procedures section herein, all samples were tested using a polar fluid composition of 0.9% sodium chloride in water. Comparative Example 1, a 100% cotton topsheet having no coating, exhibited a very short Fluid Strike-Through time, but also exhibited a very high amount of Rewet. As discussed above, it is believed that natural fibers may form hydrogen bonds with polar fluids, such as urine, that may come into contact or pass near the fibers. Thus, the polar fluids may not quickly drain completely through a topsheet comprising natural fibers, but may instead swell the fibers and remain in or on the topsheet. As demonstrated in Comparative Example 1, the polar fluid penetrated the surface of the topsheet relatively quickly (thus the short Fluid Strike-Through Time), but remained within the topsheet (as evidenced by the large amount of Rewet).

Comparative Examples 2-8 all exhibited improved Rewet amounts as compared to Comparative Example 1, but all had very significantly increased Fluid Strike-Through Times. Without wishing to be bound by theory, it is believed that the coating materials of Comparative Examples 2-8 resulted in a finished topsheet sample that was too hydrophobic and thus impaired the flow of polar fluids through the topsheet samples. The repulsive hydrophobic force exhibited by the coatings of Comparative Examples 2-8 may have inhibited the flow of polar fluid through the topsheet samples, resulting in high Fluid Strike-Through Times, but also repelled the fluids, thus preventing reentry of the fluids into the fiber matrix and resulting in reduced Rewet amounts as compared to the uncoated Comparative Example 1.

Examples 1 and 2 of the present disclosure exhibited both greatly improved Rewet amounts as well as very acceptable Fluid Strike-Through Times, as compared to Comparative Example 1. Without wishing to be bound by theory, it is believed that a topsheet comprising a composition comprising a wax ester and a polyglyceryl emulsifier may provide a semi-hydrophilic coating that allows polar fluids to pass through the topsheet, while preventing or at least inhibiting the fluid from contacting the fibers of the topsheet. Examples 1 and 2 of the present disclosure were able to achieve similar Rewet amounts as compared with Comparative Examples 2-8, but showed greatly improved Fluid Strike-Through Times as compared to Comparative Examples 2-8.

Comparative Example 9

The nonwoven topsheet described herein as Comparative Example 9 is a nonwoven web comprising 100% cotton fibers. The fibers are formed into a nonwoven web by a spunlace process. The nonwoven topsheet has a basis weight of 35 gsm. Comparative Example 9 does not have a coating.

Comparative Example 10

The nonwoven topsheet described herein as Comparative Example 10 is the nonwoven topsheet material of Comparative Example 9 and has a composition comprising interesterified jojoba wax ester (Floraester-60®) at a level of 1.0% by weight of the topsheet.

Comparative Example 11

The nonwoven topsheet described herein as Comparative Example 11 is the nonwoven topsheet material of Comparative Example 9 and has a composition comprising a 5:1 mixture, by weight, of interesterified jojoba wax ester (Floraester-60®) to polyglyceryl-2 stearate, at a level of 1.0% by weight of the topsheet.

Comparative Example 12

The nonwoven topsheet described herein as Comparative Example 12 is the nonwoven topsheet material of Comparative Example 9 and has a composition comprising a 2:1 mixture, by weight, of interesterified jojoba wax ester (Floraester-60®) to polyglyceryl-2 stearate, at a level of 1.0% by weight of the topsheet.

Example 3

The nonwoven topsheet described herein as Example 3 is the nonwoven topsheet material of Comparative Example 9 and has a composition comprising a 1.5:1 mixture, by weight, of interesterified jojoba wax ester (Floraester-60) to polyglyceryl-2 stearate, at a level of 1.0% by weight of the topsheet.

Example 4

The nonwoven topsheet described herein as Example 4 is the nonwoven topsheet material of Comparative Example 9 and has a composition comprising a 1:1 mixture, by weight, of interesterified jojoba wax ester (Floraester-60) to polyglyceryl-2 stearate, at a level of 1.0% by weight of the topsheet.

Example 5

The nonwoven topsheet described herein as Example 5 is the nonwoven topsheet material of Comparative Example 9 and has a composition comprising a 0.5:1 mixture, by weight, of interesterified jojoba wax ester (Floraester-60) to polyglyceryl-2 stearate, at a level of 1.0% by weight of the topsheet.

Comparative Example 13

The nonwoven topsheet described herein as Example 13 is the nonwoven topsheet material of Comparative Example 9 and has a composition comprising polyglyceryl-2 stearate at a level of 1.0% by weight of the topsheet.

The Comparative Examples resented in TABLE 2 were tested for Fluid Strike-Through and Rewet in duplicate. Examples 3-5 were tested for Fluid Strike-Through and Rewet in quadruplicate.

TABLE 2

Fluid handling performance of nonwoven topsheets comprising compositions of varying ratios of wax ester to polyglyceryl emulsifier.

| Example | Coating Level (% by wt. of topsheet) | Weight Ratio of jojoba wax ester to polyglyceryl-2 stearate in coating | Contact Angle (°) | Fluid Strike-Through (s) | Rewet (mg) |
|---|---|---|---|---|---|
| Comparative Example 9 | 0 | N/A | 0 | 1.6/1.5 | 525.3/563.3 |
| Comparative Example 10 | 1.0 | 1:0 | 128-135 | 403.3/372.2 | 68.9/77.8 |
| Comparative Example 11 | 1.0 | 5:1 | 125-129 | 424.8/382.5 | 73.1/79.2 |
| Comparative Example 12 | 1.0 | 2:1 | 120-128 | 304.5/192.3 | 58.3/52.6 |
| Example 3 | 1.0 | 1.5:1 | 75-95 | 9.7/11.3/ 5.1/9.5 | 41.5/37.0/ 52.3/36.9 |
| Example 4 | 1.0 | 1:1 | 65-89 | 8.2/5.3/ 7.8/6.2 | 39.6/45.5/ 58.0/40.1 |
| Example 5 | 1.0 | 0.5:1 | 67-90 | 7.2/17.7/ 11.2/8.8 | 98.2/44.5/ 50.1/46.4 |
| Comparative Example 13 | 1.0 | 0:1 | 111-118 | 47.9/37.1 | 46.3/67.4 |

Comparative Examples 10-13, as shown in TABLE 2, have Contact Angles above 100°. Examples having Contact Angles above 100° may be associated with greater Fluid Strike-Through Times, as compared to nonwoven topsheets having Contact Angles of less than 100°. Examples 3-5 of the present disclosure, which comprise a wax ester and a polyglyceryl emulsifier in a weight ratio of between about 0.5:1 and about 1.5:1, have a Contact Angle between about 65° and about 95°. Examples 3-5 also have reduced mean Fluid Strike-Through Times as compared to Comparative Examples 10-13, and a reduced mean Rewet amount as compared to Comparative Example 9.

Examples 6-19

The nonwoven topsheets described herein as Examples 6-19 are the nonwoven topsheet material of Comparative Example 9 and have a composition comprising a mixture of jojoba wax ester and polyglyceryl-2 stearate (PolyAquol™ W2). The jojoba wax ester is interesterified to achieve a melting point of about 56° C.-60° C. (Tradename Floraester®-60). The coating mixture comprises 1 part jojoba wax ester to 1 part polyglyceryl-2 stearate, and is applied to the nonwoven topsheet at a level of 1%-1.5% by weight of the topsheet. Examples 6-19 were produced on pilot scale equipment.

TABLE 3

Fluid Strike-Through times for nonwoven topsheets comprising a semi-hydrophilic coating produced at pilot scale.

| Example | Coating level (% by weight of topsheet) | Coating ingredients (wt. ratio) | Fluid Strike-Through (s) |
|---|---|---|---|
| Example 6 | 1-1.5 | Wax ester + polyglyceryl emulsifier (1:1) | 1.4 |
| Example 7 | 1-1.5 | Wax ester + polyglyceryl emulsifier (1:1) | 1.5 |
| Example 8 | 1-1.5 | Wax ester + polyglyceryl emulsifier (1:1) | 1.6 |
| Example 9 | 1-1.5 | Wax ester + polyglyceryl emulsifier (1:1) | 1.7 |
| Example 10 | 1-1.5 | Wax ester + polyglyceryl emulsifier (1:1) | 1.7 |
| Example 11 | 1-1.5 | Wax ester + polyglyceryl emulsifier (1:1) | 2.0 |
| Example 12 | 1-1.5 | Wax ester + polyglyceryl emulsifier (1:1) | 1.8 |
| Example 13 | 1-1.5 | Wax ester + polyglyceryl emulsifier (1:1) | 1.9 |
| Example 14 | 1-1.5 | Wax ester + polyglyceryl emulsifier (1:1) | 1.5 |
| Example 15 | 1-1.5 | Wax ester + polyglyceryl emulsifier (1:1) | 1.7 |
| Example 16 | 1-1.5 | Wax ester + polyglyceryl emulsifier (1:1) | 1.9 |
| Example 17 | 1-1.5 | Wax ester + polyglyceryl emulsifier (1:1) | 1.9 |
| Example 18 | 1-1.5 | Wax ester + polyglyceryl emulsifier (1:1) | 1.9 |
| Example 19 | 1-1.5 | Wax ester + polyglyceryl emulsifier (1:1) | 2.0 |

Examples 6-19 were tested for Fluid Strike-Through Time, according to the Fluid Strike-Through Test described herein. Fluid Strike-Through times remained low in the examples that comprised the semi-hydrophilic wax composition of the present disclosure, and applied to the topsheet at a level of between about 1% and about 1.5%, indicating that the coating process was effective at pilot scale.

Comparative Example 14

The nonwoven topsheet described herein as Comparative Example 14 is a nonwoven web comprising 100% cotton fibers. The fibers are formed into a nonwoven web by a spunlace process. The nonwoven topsheet has a basis weight of 35 gsm. Comparative Example 14 does not comprise a coating.

Comparative Example 15

The nonwoven topsheet described herein as Comparative Example 16 is a nonwoven web comprising 100% viscose fibers. The fibers are formed into a nonwoven web by a spunlace process. The nonwoven topsheet has a basis weight of 50 gsm. Comparative Example 16 does not comprise a coating.

Example 20

The nonwoven topsheet described herein as Example 20 is a nonwoven web comprising 100% cotton fibers. The fibers are formed into a nonwoven web by a spunlace process. The nonwoven topsheet has a basis weight of 35 gsm. The nonwoven topsheet has a composition comprising a 1:1 mixture, by weight, of interesterified jojoba wax ester (Floraester-60®) to polyglyceryl-2 stearate, at a level of 1.0% by weight of the topsheet.

Example 21

The nonwoven topsheet described herein as Example 21 is the top layer of a three-dimensional laminate made generally according to the process described in U.S. Pat. App. Publ. No. 2018/0228666 to Trinkaus et al. The nonwoven topsheet layer comprises 100% cotton fibers that are formed into a nonwoven web by a spunlace process. The nonwoven topsheet layer has a basis weight of 35 gsm. The nonwoven topsheet is delaminated from a substrate by applying a cryogenic spray to the topsheet laminate and pulling back the top layer to separate it from the underlying laminate layer. The nonwoven topsheet has a composition comprising a 1:1 mixture, by weight, of interesterified jojoba wax ester (Floraester-60®) to polyglyceryl-2 stearate, at a level of 1.0% by weight of the topsheet.

Example 22

The nonwoven topsheet described herein as Example 22 is a nonwoven web comprising 100% cotton fibers. The fibers are formed into a nonwoven web by a spunlace process. The nonwoven topsheet has a basis weight of 35 gsm. The nonwoven topsheet has a composition comprising a 0.5:1 mixture, by weight, of interesterified jojoba wax ester (Floraester-60®) to polyglyceryl-2 stearate, at a level of 1.0% by weight of the topsheet.

Example 23

The nonwoven topsheet described herein as Example 23 is a nonwoven web comprising 100% cotton fibers. The fibers are formed into a nonwoven web by a spunlace process. The nonwoven topsheet has a basis weight of 35 gsm. The nonwoven topsheet has a composition comprising a 2:1 mixture, by weight, of interesterified jojoba wax ester (Floraester-60®) to polyglyceryl-2 stearate, at a level of 1.0% by weight of the topsheet.

TABLE 4

Fiber absorption potential of various nonwoven topsheets as measured by the Fiber Wicking Test.

| Example | Topsheet | Wicking height at 10 s | Wicking height at 30 s | Wicking height at 60 s |
| --- | --- | --- | --- | --- |
| Comparative Example 14 | 35 gsm 100% Cotton, uncoated | 36.6 | 49.0 | 59.0 |
| Comparative Example 15 | 50 gsm 100% Viscos spunlace | 47.0 | 64.0 | 79.0 |
| Example 20 | 35 gsm 100% Cotton, coated (1:1) | 0.0 | 1.0 | 1.0 |
| Example 21 | 35 gsm 100% Cotton, coated (1:1), delaminated from 3D+ | 3.0 | 6.0 | 7.0 |
| Example 22 | 35 gsm 100% Cotton, coated (0.5:1) | 0.0 | 0.5 | 1.0 |
| Example 23 | 35 gsm 100% Cotton, coated (2:1) | 0.0 | 0.0 | 0.0 |

As shown in TABLE 4, non-coated topsheets comprising natural or semi-synthetic (viscose) fibers wick fluid into the fiber matrix of the topsheet over the 60 second test period at a greater rate than coated topsheets comprising natural fibers. As discussed above, the semi-hydrophilic wax composition may form a physical barrier around the fibers of the topsheet and may reduce or prevent fluid from contacting the fibers. Table 4 demonstrates that topsheets comprising a semi-hydrophilic wax composition are unable to wick fluids into the fiber matrix of the topsheet.

Method of Manufacturing Topsheets Comprising a Semi-Hydrophilic Wax Composition

Figure 18:
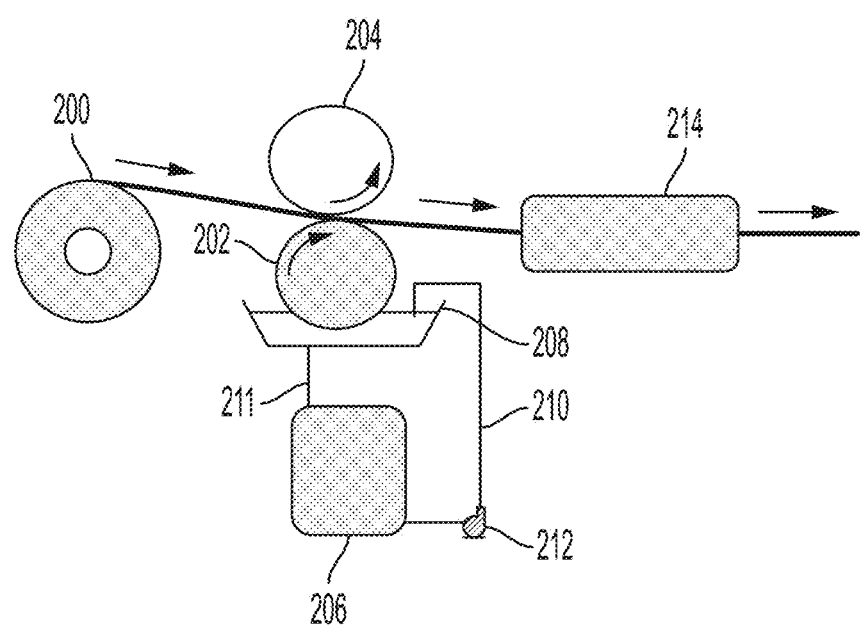
FIG. 18 is a schematic illustration of an apparatus for applying a semi-hydrophilic wax composition to a topsheet or nonwoven web.

The liquid permeable topsheets comprising natural fibers may be coated with the semi-hydrophilic composition generally by the process schematically illustrated in FIG. 18. First, a semi-hydrophilic composition emulsion may be prepared and stored in a mixing tank 206. The mixing tank 206 may comprise a high sheer agitation system capable of maintaining a semi-hydrophilic composition emulsion in water, wherein the semi-hydrophilic composition droplets have a mean droplet size of less than about 10 microns. Without wishing to be bound by theory, it is believed that an emulsion comprising semi-hydrophilic composition droplets having a mean droplet size of less than about 10 microns may result in a more homogeneous coating of the fibers. An emulsion having a mean droplet size of greater than about 10 microns may result in inconsistent application of the semi-hydrophilic composition on the fibers, potentially causing fibers to stick together and form hard spots. The mixing tank 206 may be in fluid communication with a soaking tank 208 through circulation pipes 210, 211 and a circulation pump 212, for example. The circulation pump may be a high-shear pump capable of maintaining the microemulsion of semi-hydrophilic composition in water. The mixing tank 206 and soaking tank 208 may be maintained at a temperature range of about 60° C. to about 90° C., or about 70° C. to about 85° C.

Next, a nonwoven web 200 from a spool or otherwise is fed between a mesh roll 202 and a rubber roll 204. The mesh roll 202 may comprise a plurality of small depressions or pockets engraved into the surface of the mesh roll 202. The mesh roll 202 may be heated to a temperature of between about 60° C. and about 90° C. The mesh roll 202 may be disposed so as to be at least partially submerged in the semi-hydrophilic composition emulsion in the soaking tank 208, so that, as the mesh roll 202 passes through the semi-hydrophilic composition emulsion, an amount of the emulsion may be picked up and carried in the small depressions or pockets in the surface of the mesh roll 202. The mesh roll 202 may be driven in a first direction (as indicated by the arrow) to match the feed direction of the nonwoven web 200. The compression roll 204 may comprise a resilient or compressible surface, such as, for example, rubber. As the nonwoven web is fed between the mesh roll 202 and the compression roll 204, the compression roll 204 may bring the nonwoven web 200 into contact with the mesh roll 202, and the semi-hydrophilic composition emulsion contained within the small depressions or pockets engraved into the surface of the mesh roll 202. Upon contact of the nonwoven web 200 with the semi-hydrophilic composition emulsion, the emulsion may adsorb to the surface of the material web 200, or to the surface of the fibers of the nonwoven web 200. The material web 200 may then fed into a drying oven 214, such as a through-air drying oven, for example. The drying oven may be maintained at a temperature of between about 120° C. and about 150° C.

Test Procedures
Fluid Strike-Through Test:

Fluid Strike-Through is measured according to the WSP 70.3-08 standard test method for nonwoven Fluid Strike-Through.

If a topsheet is available in its raw material form, a specimen 125 mm±0.5 mm in length and 125 mm±0.5 mm wide is cut from the raw material according to WSP 70.3-08. Otherwise, a topsheet specimen is removed from the absorbent article, centered at the intersection of the longitudinal and lateral centerlines of the absorbent article. For the purposes of removing the topsheet from the absorbent article, a razorblade is used to excise the topsheet from the underlying layers of the absorbent article around the outer perimeter of the 125 mm±0.5 mm area. In cases where the topsheet comprises multiple layers of nonwoven material, only the top (user-facing) layer of the multi-layer topsheet serves as the specimen. The specimen is carefully removed such that its longitudinal and lateral extension are maintained. A cryogenic spray (such as Cyto-Freeze, Control Company, Houston, Tex.) can be used to remove the topsheet specimen from the underlying layers, if necessary. One layer of topsheet material is used for this test. The one layer topsheet material sample is placed on five plies of Ahlstrom-Munksio grade 989 (Ahlstrom-Munksio, Helsinki, Finland) filter paper or equivalent. The LISTER AC instrument (Lenzing Instruments, Gampern, Austria) or equivalent is used for the Fluid Strike-Through Test. The Fluid Strike-Through Test is performed in duplicate on two like specimens, and the arithmetic mean of the two results is reported to the nearest 0.1 second as the Fluid Strike-Through.

Rewet Test:

The Rewet Test is used to determine Rewet Value and is performed on two specimens having first been characterized by the Fluid Strike-Through Test. Laboratory conditions are the same as in the Fluid Strike-Through Test (that is, as specified by WSP 70.3-08).

For each specimen analyzed, first one layer of filter paper (Ahlstrom grade 632 filter paper, Ahlstrom-Munksio, Helsinki, Finland, or equivalent) is pre-weighed, and its mass is recorded as M1 to the nearest 0.1 mg.

Figure 19:
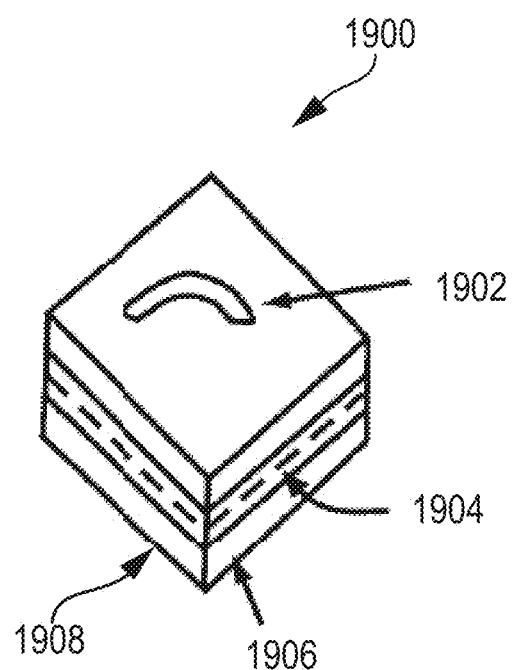
FIG. 19 is a schematic illustration of an SBW weight.

Immediately after the Fluid Strike-Through Test is performed on the specimen, the baseplate with the specimen and five-ply filter paper stack are removed from the Strike-Through apparatus used in the Fluid Strike-Through Test. The pre-weighed single layer of filter paper, defined as the pick-up paper, is placed on top of the topsheet sample. A weight is placed on top of the pick-up paper and topsheet for 120 seconds. FIG. 19 is a schematic illustration of the weight 1900. The weight 1900 comprises a weight 1902 with a 10 cm×10 cm stainless steel base and a handle, with a total mass of 4000 g±20 g. Tape 1904 is placed on the underside of the base of the weight. Polyurethane foam rubber 1906 with dimensions of 10 cm×10 cm×2 cm is affixed to the tape 1904. A polyethylene film 1908 with dimensions 10 cm×10 cm×25 μm is then attached to the underside of the polyurethane foam rubber 1906. After 120 seconds, the pick-up paper is removed from the topsheet sample and weighed again, the mass recorded to the nearest 0.1 mg as M2. The Rewet mass for the specimen is defines as M2-M1. The arithmetic mean of the Rewet masses of two like specimen replicates is defines as the Rewet Value and is reported to the nearest 0.1 mg.

Iodine Value Test:

The Iodine Value of a composition is determined using the American Oil Chemists' Society (AOCS) standard test method Cd 1d-92.

Contact Angle Test:

The Contact Angle Test is used to measure the contact angle made by highly purified water (18 M Ω-cm) in contact with constituent fibers of a sample nonwoven. All measurements are performed at an ambient temperature of 24±2° C. Raw material nonwoven is analyzed as received without compression, and nonwoven in a finished article is excised as received in the article. Six representative nonwoven specimen areas measuring approximately 5 cm±0.5 cm in length and 5 cm±0.5 cm wide are excised from a nonwoven of interest, and each is analyzed sequentially using a DataPhysics OCA 50 controlled via TP50 (DataPhysics Instruments GmbH, Filderstadt, Germany) or equivalent. 2 μL of highly purified water are placed on the nonwoven specimen surface, and the camera (operating at 20 frames/second) is used to capture the droplet shape on the nonwoven surface. Time zero is defined as the first frame in which the droplet is observed to touch the nonwoven surface, and the frame at 5.0 seconds is captured and further analyzed using the instrument's software to determine the contact angle between the droplet and a fiber on the nonwoven surface. In this analysis, the baseline of the fiber is identified manually, and the Laplace-Young fitting mode is used to determine the contact angle. Six like specimens are analyzed and the arithmetic mean of the six individual contact angle results is calculated and reported to the nearest integer degree as the Contact Angle of the sample nonwoven.

Fiber Wicking Test:

Fiber Wicking is measured according to the EDANA 10.4-02 standard test method for nonwovens. The purpose of the Fiber Wicking Test is to characterize the ability of a nonwoven web to wick liquid vertically.

A nonwoven web is cut into test pieces 30±1 mm wide and 250±1 mm long. In cases where a topsheet comprises multiple layers of nonwoven material, only the top (user-facing) layer of the multi-layer topsheet serves as the specimen. Two holes, each 5±1 mm in diameter, are punched out of a short end of each test piece at 5±1 mm from the short and long side. The test liquid is 0.9% NaCl solution.

Figure 20:
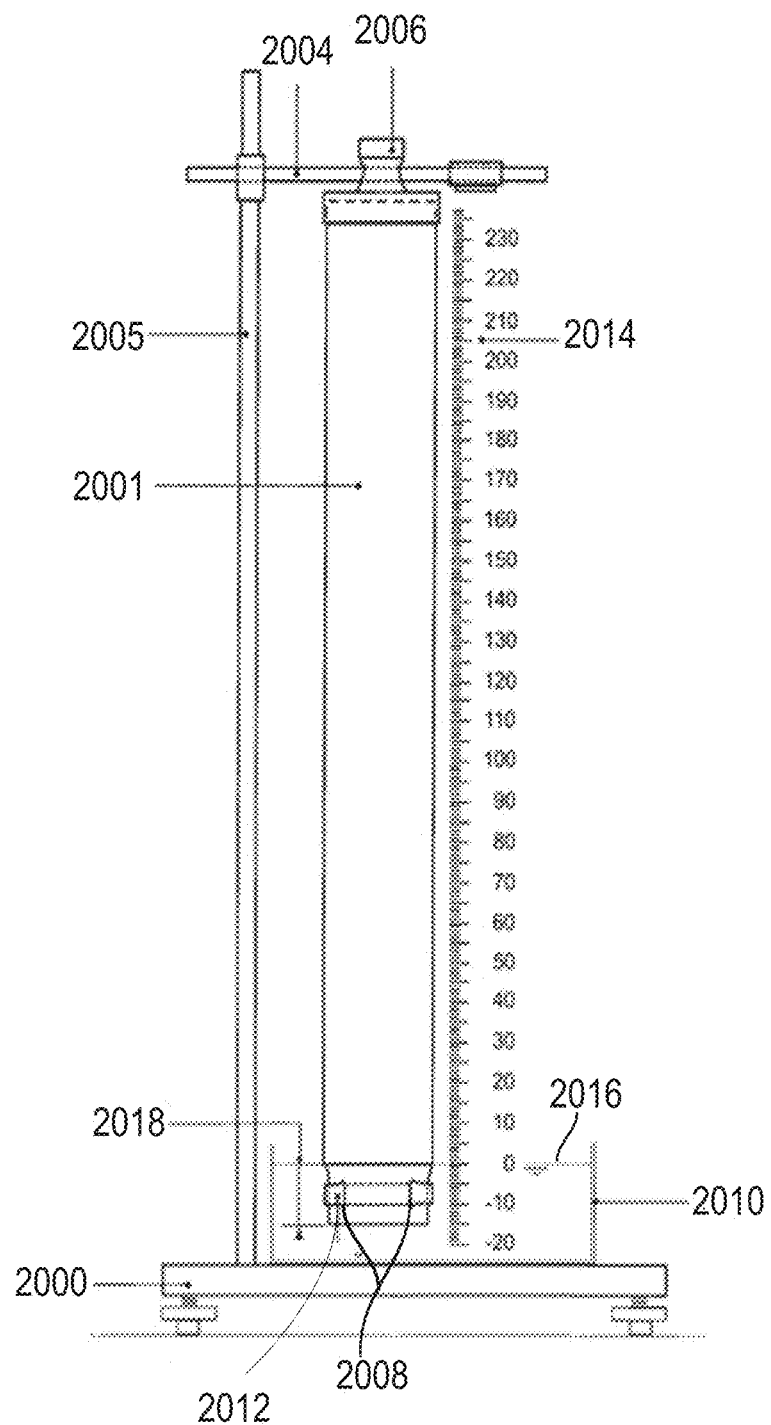
FIG. 20 is a schematic illustration of an apparatus for conducting the Fiber Wicking Test disclosed herein.

FIG. 20 is a schematic illustration of an apparatus for conducting the Fiber Wicking Test. A test sample 2001 is clamped vertically to the horizontal support 2004 using a clamp 2006, with the punched holes 2008 at the end away from the clamp 2006. The horizontal support 2004 is movably attached to a vertical support 2005, that is securely fastened to a base 2000. A glass rod 2012 is inserted through the two holes 2008 to tension the test sample and to allow the test sample to remain vertical. A ruler 2014 is clamped to the horizontal support 2004 next to the test sample 2001. The test sample 2001 is positioned parallel to the ruler 2014 so that the test sample 2001 projects 15 mm±2 mm below the zero mark of the measuring rod 2014. A reservoir 2010 containing the test liquid 2016 is placed under the test sample 2001 so that the test sample 2001 is suspended above, but not contacting, the test liquid 2016.

To begin the test procedure, the horizontal support 2004 is lowered so that the zero mark of the ruler 2014 is at the surface of the test liquid 2016. The lower edge 2018 of the test sample 2001 will be 15 mm±2 mm below the surface of the test liquid 2016. Once the test sample 2001 is in position, a stopwatch is started. The height of the liquid on the test sample 2001 is recorded after 10 seconds, 30 seconds, and 60 seconds. If the height of the liquid on the test sample 2001 is not uniform across the test sample 2001, then record the highest point at which the liquid has reached at each time point. Report results to the nearest 0.1 mm.

EXAMPLES/COMBINATIONS

A. An absorbent article comprising:
a liquid permeable nonwoven topsheet comprising:
natural fibers;
a first side and an opposing second side; and
a semi-hydrophilic wax composition disposed on the first side and/or the second side of the nonwoven topsheet and comprising a wax ester and a polyglyceryl emulsifier, wherein a weight ratio of the wax ester to the polyglyceryl emulsifier is between about 1.5:1 and about 0.5:1, and preferably between about 1.25:1 and about 0.75:1;
a liquid impermeable backsheet; and
an absorbent core disposed at least partially between the nonwoven topsheet and the backsheet.

B. An absorbent article comprising:
a liquid permeable nonwoven topsheet comprising:
natural fibers;
a first side and an opposing second side; and
a semi-hydrophilic wax composition comprising a wax ester and a polyglyceryl emulsifier disposed between the first side and the second side of the nonwoven topsheet, wherein a weight ratio of the wax ester to the polyglyceryl emulsifier is between about 1.5:1 and about 0.5:1, and preferably between about 1.25:1 and about 0.75:1;
a liquid impermeable backsheet; and
an absorbent core disposed at least partially between the nonwoven topsheet and the backsheet.

C. An absorbent article comprising:
a liquid permeable nonwoven topsheet comprising:
natural fibers;
a first side and an opposing second side; and
a semi-hydrophilic wax composition disposed on a surface of a portion of the natural fibers and comprising a wax ester and a polyglyceryl emulsifier;
wherein a weight ratio of the wax ester to the polyglyceryl emulsifier is between about 1.5:1 and about 0.5:1, and preferably between about 1.25:1 and about 0.75:1;
a liquid impermeable backsheet; and
an absorbent core disposed at least partially between the nonwoven topsheet and the backsheet.

D. An absorbent article comprising:
a liquid permeable nonwoven topsheet comprising natural fibers;
a liquid impermeable backsheet;
an absorbent core disposed at least partially between the nonwoven topsheet and the backsheet; and
a semi-hydrophilic wax composition disposed on a surface of a portion of the natural fibers and comprising a wax ester and a polyglyceryl emulsifier;
wherein a weight ratio of the wax ester to the polyglyceryl emulsifier is between about 1.5:1 and about 0.5:1, and preferably between about 1.25:1 and about 0.75:1; and
wherein the semi-hydrophilic wax composition is disposed at least on the surface of the natural fibers by a process comprising the steps of:
melting the semi-hydrophilic wax composition;
dispersing the semi-hydrophilic wax composition in a continuous phase to form droplets of the semi-hydrophilic wax composition with a mean droplet size of less than 10 microns;
exposing the nonwoven topsheet to the melted semi-hydrophilic wax composition dispersion; and
drying the semi-hydrophilic wax coated nonwoven topsheet.

E. The absorbent article of any one of the preceding paragraphs, wherein the nonwoven topsheet comprises between about 20% and about 100%, preferably between about 50% and about 100%, and more preferably between about 65% and 100%, by weight of the nonwoven topsheet, of the natural fibers.

F. The absorbent article of any one of the preceding paragraphs, wherein the natural fibers comprise plant fibers.

G. The absorbent article of paragraph F, wherein the plant fibers comprise cotton fibers.

H. The absorbent article of any one of the preceding paragraphs, wherein the semi-hydrophilic wax composition is distributed generally equally throughout the nonwoven topsheet.

I. The absorbent article of any one of the preceding paragraphs, wherein the wax ester comprises between about 32 to about 48 carbon atoms per molecule of the wax ester.

J. The absorbent article of any one of the preceding paragraphs, wherein the wax ester has an iodine value of between about 35 g/100 g and about 50 g/100 g, preferably between about 38 g/100 g and about 48 g/100 g, and more preferably between about 40 g/100 g and about 44 g/100 g, according to the Iodine Value Test.

K. The absorbent article of any one of the preceding paragraphs, wherein the semi-hydrophilic wax composition has a melting temperature of between about 35° C. and about 80° C., preferably between about 45° C. and about 70° C., and more preferably between about 50° C. and about 60° C.

L. The absorbent article of any one of the preceding paragraphs, wherein the wax ester is a natural wax ester.

M. The absorbent article of any one of the preceding paragraphs, wherein the wax ester is jojoba wax ester.

N. The absorbent article of any one of the preceding paragraphs, wherein the polyglyceryl emulsifier is polyglyceryl-2-stearate.

O. The absorbent article of any one of the preceding paragraphs, wherein the nonwoven topsheet comprises between about 0.5% and about 1.5%, and preferably between about 0.75% and about 1.25%, by weight of the nonwoven topsheet of the semi-hydrophilic wax composition.

P. The absorbent article of any one of the preceding paragraphs, wherein the semi-hydrophilic wax composition is insoluble in water.

Q. The absorbent article of any one of the preceding paragraphs, wherein the nonwoven topsheet has a Contact Angle of between about 35 and about 100°, and preferably between about 450 and about 95°, according to the Contact Angle Test.

R. The absorbent article of any one of the preceding paragraphs, wherein the nonwoven topsheet has a Fluid Strike-Through time of between about 0.5 second to about 18 seconds, preferably between about 0.5 seconds and about 12 seconds, and more preferably between about 1 second and about 5 seconds, according to the Fluid Strike-Through Test.

S. The absorbent article of any one of the preceding paragraphs, wherein the nonwoven topsheet has a Rewet value of between about 1 mg and about 100 mg, and preferably between about 5 mg and about 85 mg, according to the Rewet Test.

T. The absorbent article of any one of the preceding paragraphs, wherein the nonwoven topsheet comprises 100% cotton fibers, and wherein the nonwoven topsheet has a basis weight of about 20 to about 45 gsm.

U. The absorbent article of any one of the preceding paragraphs, wherein the semi-hydrophilic wax composition comprises two layers on a surface of the nonwoven topsheet, wherein each layer comprises a high polarity portion and a low polarity portion, wherein the high polarity portion of a layer most proximal to the natural fibers faces the natural fibers, and wherein the high polarity portion of a layer most distal from the natural fibers forms an outermost portion of the surface of the nonwoven topsheet.

V. An absorbent article comprising:
 a liquid permeable nonwoven topsheet comprising: natural fibers, a first side, a second side, and a semi-hydrophilic composition, wherein the nonwoven topsheet has a Fluid Strike-Through time of between about 0.5 second to about 18 seconds, preferably between about 0.5 seconds and about 12 seconds, and more preferably between about 1 second and about 5 seconds, according to the Fluid Strike-Through Test, and wherein the nonwoven topsheet has a wicking height of between about 0 mm and about 10 mm, preferably between about 0 mm and about 7 mm, and more preferably between about 0 mm and about 5 mm, according to the Topsheet Wicking Test;
 a liquid impermeable backsheet; and
 an absorbent core disposed at least partially between the nonwoven topsheet and the backsheet.

W. The absorbent article of paragraph V, wherein the semi-hydrophilic composition is disposed on a portion of the natural fibers.

X. The absorbent article of paragraph V, wherein the semi-hydrophilic wax composition is disposed at least on fibers intermediate the first side and the second side of the nonwoven topsheet.

Y. The absorbent article of paragraph V, wherein the semi-hydrophilic composition is distributed generally equally throughout the nonwoven topsheet.

Z. The absorbent article of any one of paragraphs V-Y, wherein the semi-hydrophilic comprises a wax ester and a polyglyceryl emulsifier.

AA. The absorbent article of paragraph Z, wherein a weight ratio of the wax ester to the polyglyceryl emulsifier is between about 1.5:1 and about 0.5:1, and preferably between about 1.25:1 and about 0.75:1

BB. The absorbent article of any one of paragraphs Z and AA, wherein the polyglyceryl emulsifier comprises polyglyceryl-2-stearate.

CC. The absorbent article of any one of paragraphs Z-BB, wherein the wax ester has an iodine value of between about 35 g/100 g and about 50 g/100 g, preferably between about 38 g/100 g and about 48 g/100 g, and more preferably between about 40 g/100 g and about 44 g/100 g, according to the Iodine Value Test.

DD. The absorbent article of any one of paragraphs Z-CC, wherein the wax ester comprises between about 32 to about 48 carbon atoms per molecule of the wax ester.

EE. The absorbent article of any one of paragraphs V-DD, wherein the semi-hydrophilic composition has a melting temperature of between about 35° C. and about 80° C., preferably between about 45° C. and about 70° C., and more preferably between about 50° C. and about 60° C.

FF. The absorbent article of any one of paragraphs V-EE, wherein the semi-hydrophilic composition is insoluble in water.

GG. The absorbent article of any one of paragraphs V-FF, wherein the nonwoven topsheet has a Contact Angle of between about 35 and about 100°, and preferably between about 45° and about 95°, according to the Contact Angle Test.

HH. The absorbent article of any one of paragraphs V-GG, wherein the nonwoven topsheet has a Rewet value of between about 1 mg and about 100 mg, and preferably between about 5 mg and about 85 mg, according to the Rewet Test.

An absorbent article of the present disclosure may comprise a liquid permeable nonwoven topsheet comprising: between about 20% and about 100%, preferably between about 50% and about 100%, and more preferably between about 65% and about 100%, by weight of the nonwoven topsheet, of the natural fibers; a first side and an opposing second side; and a semi-hydrophilic wax composition disposed on the first side and/or the second side of the nonwoven topsheet and comprising a wax ester and a polyglyceryl emulsifier, wherein a weight ratio of the wax ester to the polyglyceryl emulsifier is between about 1.5:1 and about 0.5:1, and preferably between about 1.25:1 and about 0.75:1. The absorbent article may further comprise a liquid impermeable backsheet, an outer-cover nonwoven in a facing relationship with the backsheet, and an absorbent core disposed at least partially between the nonwoven topsheet and the backsheet. The natural fibers of the topsheet may comprise cotton fibers. The wax ester of the semi-hydrophilic wax composition may comprise a natural wax ester. The natural wax ester may be jojoba wax ester. The polyglyceryl emulsifier may be polyglyceryl-2-stearate. The semi-hydrophilic wax composition comprises two layers on a surface of the nonwoven topsheet, wherein each layer comprises a high polarity portion and a low polarity portion, wherein the high polarity portion of a layer most proximal to the natural fibers faces the natural fibers, and wherein the high polarity portion of a layer most distal from the natural fibers forms an outermost portion of the surface of the nonwoven topsheet.

An absorbent article of the present disclosure may comprise a liquid permeable nonwoven topsheet comprising: between about 20% and about 100%, preferably between about 50% and about 100%, and more preferably between about 65% and about 100%, by weight of the nonwoven topsheet, of the natural fibers; a first side and an opposing second side; and a semi-hydrophilic wax composition comprising a wax ester and a polyglyceryl emulsifier disposed between the first side and the second side of the nonwoven topsheet, wherein a weight ratio of the wax ester to the polyglyceryl emulsifier is between about 1.5:1 and about 0.5:1, and preferably between about 1.25:1 and about 0.75:1. The absorbent article may further comprise a liquid impermeable backsheet, a pair of barrier leg cuffs, each barrier leg cuff comprising an elastic member, and an absorbent core disposed at least partially between the nonwoven topsheet and the backsheet. The natural fibers of the topsheet may comprise cotton fibers. The wax ester of the semi-hydrophilic wax composition may comprise a natural wax ester. The natural wax ester may be jojoba wax ester. The polyglyceryl emulsifier may be polyglyceryl-2-stearate. The semi-hydrophilic wax composition comprises two layers on a surface of the nonwoven topsheet, wherein each layer comprises a high polarity portion and a low polarity portion, wherein the high polarity portion of a layer most proximal to the natural fibers faces the natural fibers, and wherein the high polarity portion of a layer most distal from the natural fibers forms an outermost portion of the surface of the nonwoven topsheet.

An absorbent article of the present disclosure may comprise a liquid permeable nonwoven topsheet comprising: between about 20% and about 100%, preferably between about 50% and about 100%, and more preferably between about 65% and 100%, by weight of the nonwoven topsheet, of the natural fibers; a first side and an opposing second side; and a semi-hydrophilic wax composition disposed on a surface of a portion of the natural fibers and comprising a wax ester and a polyglyceryl emulsifier; wherein a weight ratio of the wax ester to the polyglyceryl emulsifier is between about 1.5:1 and about 0.5:1, and preferably between about 1.25:1 and about 0.75:1. The absorbent article may further comprise liquid impermeable backsheet, an outer-cover nonwoven in a facing relationship with the backsheet, a pair of barrier leg cuffs, each barrier leg cuff comprising an elastic member, and an absorbent core disposed at least partially between the nonwoven topsheet and the backsheet. The natural fibers of the topsheet may comprise cotton fibers. The wax ester of the semi-hydrophilic wax composition may comprise a natural wax ester. The natural wax ester may be jojoba wax ester. The polyglyceryl emulsifier may be polyglyceryl-2-stearate. The semi-hydrophilic wax composition comprises two layers on a surface of the nonwoven topsheet, wherein each layer comprises a high polarity portion and a low polarity portion, wherein the high polarity portion of a layer most proximal to the natural fibers faces the natural fibers, and wherein the high polarity portion of a layer most distal from the natural fibers forms an outermost portion of the surface of the nonwoven topsheet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. An absorbent article comprising:
    a liquid permeable nonwoven topsheet comprising:
        natural fibers;
        a first wearer-facing side and an opposing second garment-facing side; and
        a semi-hydrophilic wax composition disposed on the first side and the second side of the nonwoven topsheet and comprising a wax ester and a polyglyceryl emulsifier, wherein a weight ratio of the wax ester to the polyglyceryl emulsifier is between about 1.5:1 and about 0.5:1, wherein the semi-hydrophilic wax composition is distributed generally equally throughout the nonwoven topsheet on the first wearer-facing side and the opposing second garment-facing side;
    a liquid impermeable backsheet; and
    an absorbent core disposed at least partially between the nonwoven topsheet and the backsheet.

2. The absorbent article of claim 1, wherein the nonwoven topsheet comprises between about 20% and about 100%, by weight of the nonwoven topsheet, of the natural fibers.

3. The absorbent article of claim 2, wherein the natural fibers comprise plant fibers.

4. The absorbent article of claim 3, wherein the plant fibers comprise cotton fibers.

5. The absorbent article of claim 1, wherein the wax ester comprises between about 32 to about 48 carbon atoms per molecule of the wax ester.

6. The absorbent article of claim 1, wherein the wax ester has an iodine value of between about 35 g/100 g and about 50 g/100 g, according to the Iodine Value Test.

7. The absorbent article of claim 1, wherein the semi-hydrophilic wax composition has a melting temperature of between about 35° C. and about 80° C.

8. The absorbent article of claim 1, wherein the wax ester is a natural wax ester.

9. The absorbent article of claim 8, wherein the wax ester is jojoba wax ester.

10. The absorbent article of claim 1, wherein the polyglyceryl emulsifier is polyglyceryl-2-stearate.

11. The absorbent article of claim 1, wherein the nonwoven topsheet comprises between about 0.5% and about 1.5%, by weight of the nonwoven topsheet, of the semi-hydrophilic wax composition.

12. The absorbent article of claim 1, wherein the semi-hydrophilic wax composition is insoluble in water.

13. The absorbent article of claim 1, wherein the nonwoven topsheet has a Contact Angle of between about 35° and about 100, according to the Contact Angle Test.

14. The absorbent article of claim 1, wherein the nonwoven topsheet has a Fluid Strike-Through time of between about 0.5 second to about 18 seconds, according to the Fluid Strike-Through Test.

15. The absorbent article of claim 1, wherein the nonwoven topsheet has a Rewet value of between about 1 mg and about 100 mg, according to the Rewet Test.

16. The absorbent article of claim 1, wherein the nonwoven topsheet comprises 100% cotton fibers, and wherein the nonwoven topsheet has a basis weight of about 20 to about 45 gsm.

17. The absorbent article of claim 1, wherein the semi-hydrophilic wax composition comprises two layers on a surface of the nonwoven topsheet, wherein each layer comprises a high polarity portion and a low polarity portion, wherein the high polarity portion of a layer most proximal to the natural fibers faces the natural fibers, and wherein the high polarity portion of a layer most distal from the natural fibers forms an outermost portion of the surface of the nonwoven topsheet.

18. An absorbent article comprising:
a liquid permeable nonwoven topsheet comprising:
  natural fibers;
  a first wearer-facing side and an opposing second garment-facing side; and
  a semi-hydrophilic wax composition comprising a wax ester and a polyglyceryl emulsifier disposed on the first side of the nonwoven topsheet, on the second side of the non-woven topsheet, and between the first side and the second side of the nonwoven topsheet, wherein a weight ratio of the wax ester to the polyglyceryl emulsifier is between about 1.5:1 and about 0.5:1;
a liquid impermeable backsheet; and
an absorbent core disposed at least partially between the nonwoven topsheet and the backsheet; and
wherein the semi-hydrophilic wax composition is applied to the nonwoven topsheet at a rate of between about 0.5% and about 1.5% by weight of the nonwoven topsheet, wherein the semi-hydrophilic wax composition is distributed generally equally throughout the nonwoven topsheet on the first wearer-facing side and the opposing second garment-facing side.

19. An absorbent article comprising:
a liquid permeable nonwoven topsheet comprising:
  natural fibers;
  a first wearer-facing side and an opposing second garment-facing side; and
  a semi-hydrophilic wax composition disposed on a surface of a portion of the natural fibers located on both the first side and the second side of the topsheet and comprising a wax ester and a polyglyceryl emulsifier;
  wherein a weight ratio of the wax ester to the polyglyceryl emulsifier is between about 1.5:1 and about 0.5:1, wherein the semi-hydrophilic wax composition is distributed generally equally throughout multiple layers of the nonwoven topsheet;
a liquid impermeable backsheet; and
an absorbent core disposed at least partially between the nonwoven topsheet and the backsheet.

20. The absorbent article of claim 19, wherein the polyglyceryl emulsifier comprises polyglyceryl-2-stearate; wherein the wax ester comprises a natural wax ester; and wherein the nonwoven topsheet has a Contact Angle of between about 35° and about 100°, according to the Contact Angle Test.

\* \* \* \* \*